(12) United States Patent
Hughes et al.

(10) Patent No.: US 10,752,599 B2
(45) Date of Patent: Aug. 25, 2020

(54) CRYSTALLINE (2S,4R)-5-(5'-CHLORO-2'-FLUORO-[1,1'-BIPHENYL]-4-YL)-2-(ETHOXYMETHYL)-4-(3-HYDROXYISOXAZOLE-5-CARBOXAMIDO)-2-METHYLPENTANOIC ACID AND USES THEREOF

(71) Applicant: THERAVANCE BIOPHARMA R&D IP, LLC, South San Francisco, CA (US)

(72) Inventors: Adam D. Hughes, Half Moon Bay, CA (US); Melissa Fleury, Brisbane, CA (US); Miroslav Rapta, San Carlos, CA (US); Venkat R. Thalladi, Foster City, CA (US); Gene Timothy Fass, San Bruno, CA (US); Michael Simeone, San Francisco, CA (US)

(73) Assignee: Theravance Biopharma R&D IP, LLC, South San Francisco, CA (US)

(*) Notice: Subject to any disclaimer, the term of this patent is extended or adjusted under 35 U.S.C. 154(b) by 0 days.

(21) Appl. No.: 16/582,051

(22) Filed: Sep. 25, 2019

(65) Prior Publication Data
US 2020/0157061 A1    May 21, 2020

Related U.S. Application Data

(62) Division of application No. 16/125,991, filed on Sep. 10, 2018, now Pat. No. 10,472,335, which is a division of application No. 15/452,333, filed on Mar. 7, 2017, now Pat. No. 10,100,021.

(60) Provisional application No. 62/346,336, filed on Jun. 6, 2016, provisional application No. 62/305,393, filed on Mar. 8, 2016.

(51) Int. Cl.
| | | |
|---|---|---|
| *C07D 261/18* | (2006.01) | |
| *A61K 31/415* | (2006.01) | |
| *A61K 45/06* | (2006.01) | |
| *A61K 9/48* | (2006.01) | |
| *A61K 9/00* | (2006.01) | |

(52) U.S. Cl.
CPC .......... *C07D 261/18* (2013.01); *A61K 9/0053* (2013.01); *A61K 9/4816* (2013.01); *A61K 31/415* (2013.01); *A61K 45/06* (2013.01); *C07B 2200/13* (2013.01)

(58) Field of Classification Search
None
See application file for complete search history.

(56) References Cited

U.S. PATENT DOCUMENTS

| | | |
|---|---|---|
| 4,189,604 A | 2/1980 | Umezawa et al. |
| 4,206,232 A | 6/1980 | Ondetti et al. |
| 4,374,829 A | 2/1983 | Harris et al. |
| 4,513,009 A | 4/1985 | Roques et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |

(Continued)

FOREIGN PATENT DOCUMENTS

WO    2011/088797 A1    7/2011

OTHER PUBLICATIONS

Ksander et al., "Dicarboxylic acid dipeptide neutral endopeptidase inhibitors", Journal of Medicinal Chemistry, 38(10): 1689-1700 0995).

(Continued)

*Primary Examiner* — Kamal A Saeed
(74) *Attorney, Agent, or Firm* — Jeffrey A. Hagenah; Timothy R. Welch

(57) ABSTRACT

In one aspect, the invention relates to a crystalline form of the structure:

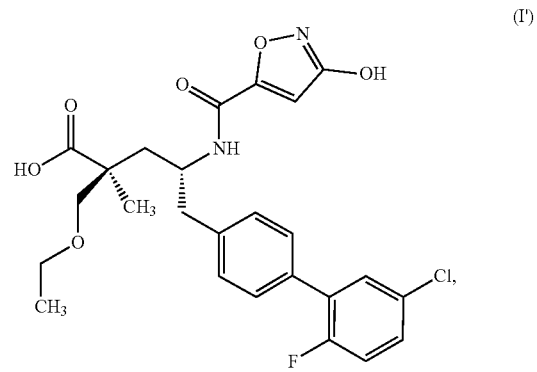

(I')

or a pharmaceutically acceptable salt thereof, having neprilysin inhibition activity. In another aspect, the invention relates to pharmaceutical compositions comprising this crystalline form; methods of using this crystalline form and its soluble form (I); and processes for preparing soluble (I) and crystalline (I') forms.

20 Claims, 6 Drawing Sheets

(56) References Cited

U.S. PATENT DOCUMENTS

| | | |
|---|---|---|
| 8,586,536 B2 | 11/2013 | Gendron et al. |
| 8,686,184 B2 | 4/2014 | Fleury et al. |
| 8,691,868 B2 | 4/2014 | Hughes et al. |
| 8,871,792 B2 | 10/2014 | Hughes et al. |
| 9,045,443 B2 | 6/2015 | Mammen et al. |
| 9,108,934 B2 | 8/2015 | Hughes et al. |
| 9,126,956 B2 | 9/2015 | Fleury et al. |
| 9,670,186 B2 | 6/2017 | Fleury et al. |
| 9,873,685 B2 | 1/2018 | Fleury et al. |
| 10,100,021 B2 | 10/2018 | Hughes et al. |
| 10,189,823 B2 | 1/2019 | Fleury et al. |
| 10,472,335 B2 | 11/2019 | Hughes et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0309724 A1 | 12/2012 | Fleury et al. |
| 2019/0276442 A1 | 9/2019 | Fleury et al. |

OTHER PUBLICATIONS

Misawa et al., "Structure-based design of dipeptide derivatives for the human neutral endopeptidase", BioOrganic & Medicinal Chemistry, 19: 5935-5947 (2011).

PCT International Search Report for PCT/US2013/053956 dated Sep. 25, 2013.

PCT International Search Report for PCT/US2017/021172.

PCT International Preliminary Report for PCT/US2017/021172 dated Jul. 6 2018.

PCT Written Opinion of the ISA for PCT/US2017/021172.

PCT Written Opinion of the IPEA for PCT/US2017/021172 dated Mar. 14 2018.

U.S. Appl. No. 16/739,525 (Fleury et al.) filed Jan. 10, 2020 (Unpublished).

CRYSTALLINE (2S,4R)-5-(5'-CHLORO-2'-FLUORO-[1,1'-BIPHENYL]-4-YL)-2-(ETHOXYMETHYL)-4-(3-HYDROXYISOXAZOLE-5-CARBOXAMIDO)-2-METHYLPENTANOIC ACID AND USES THEREOF

CROSS-REFERENCE TO RELATED APPLICATIONS

This application is a division of U.S. application Ser. No. 16/125,991, filed on Sep. 10, 2018, now U.S. Pat. No. 10,472,335; which is a division of U.S. application Ser. No. 15/452,333, filed on Mar. 7, 2017, now U.S. Pat. No. 10,100,021; which claims the benefit of U.S. Provisional Application Nos. 62/305,393 and 62/346,336, filed on Mar. 8, 2016 and Jun. 6, 2016, respectively, the entire disclosures of which are incorporated herein by reference.

BACKGROUND OF THE INVENTION

Field of the Invention

The present invention relates to a novel crystalline form having neprilysin-inhibition activity. The invention also relates to pharmaceutical compositions comprising compound, processes for preparing compound, and methods of using compound to treat diseases such as hypertension, heart failure, and renal disease.

State of the Art

Neprilysin (neutral endopeptidase, EC 3.4.24.11) (NEP), is an endothelial membrane bound $Zn^{2+}$metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

Numerous NEP inhibitors are described in U.S. Pat. No. 9,126,956 to Fleury et al. Many of these compounds have one or more desirable properties. To effectively use a NEP inhibitor compound as a therapeutic agent, however, it would be desirable to have a solid-state form that can be readily manufactured and that has acceptable chemical and physical stability. For example, it would be highly desirable to have a physical form that is thermally stable at reasonably high temperature, thereby facilitating processing and storage of the material, and a small crystal size that increases dissolution, bioavailability and absorption, thereby allowing favorable drug delivery characteristics. Crystalline solids are generally preferred over amorphous forms, for enhancing purity and stability of the manufactured product. However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use as pharmaceutical agents. Accordingly, a need exists for a stable, crystalline form which has a reasonably high melting point and a small crystal size.

SUMMARY OF THE INVENTION

The present invention provides a novel crystalline form of Compound I, which has been found to possess neprilysin (NEP) enzyme inhibition activity. Accordingly, this compound is expected to be useful and advantageous as a therapeutic agent for treating conditions such as hypertension, pulmonary hypertension, heart failure and renal disease. The structure of Compound I is:

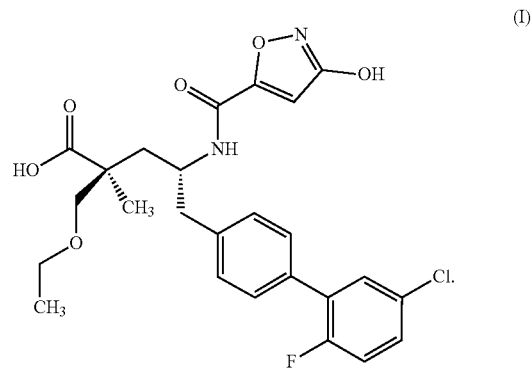 [SMILES: CCOC[C@](C)(C[C@@H](Cc1ccc(-c2cc(Cl)ccc2F)cc1)NC(=O)c1cc(O)no1)C(=O)O]

(I)

One aspect of the invention relates to a crystalline free acid form of (2S,4R)-5-(5'-chloro-2-fluoro-[1,1'-biphenyl]-4-yl)-2-(ethoxymethyl)-4-(3-hydroxyisoxazole-5-carboxamido)-2-methylpentanoic acid (Compound I'). In one embodiment, Compound I' is anhydrous, non-hygroscopic or both. Compound I' may also be referred to as crystalline form I'.

Another aspect of the invention relates to pharmaceutical compositions comprising one or more pharmaceutically acceptable carriers and Compound I'. Such compositions may optionally contain other therapeutic agents, including but not limited to, an $AT_1$ receptor antagonist, an angiotensin-converting enzyme inhibitor, a phosphodiesterase (PDE) inhibitor, a renin inhibitor, a diuretic, or combinations thereof.

Compound I' of the invention possesses NEP enzyme inhibition activity, and is therefore expected to be useful as a therapeutic agent for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of Compound I'.

Another aspect of the invention relates to a method of treating hypertension, pulmonary hypertension, heart failure, or renal disease, comprising administering to a subject a therapeutically effective amount of Compound I'. Still another aspect of the invention relates to a method for inhibiting a NEP enzyme in a subject comprising administering to the subject, a NEP enzyme-inhibiting amount of Compound I'.

Yet another aspect of the invention relates to processes useful for preparing Compound I and its crystalline form, Compound I'.

Yet another aspect of the invention relates to the use of Compound I and its crystalline form, Compound I', for the manufacture of a medicament, especially for the manufacture of a medicament useful for treating hypertension, heart failure, or renal disease. Another aspect of the invention relates to use of Compound I or Compound I' for inhibiting a NEP enzyme in a subject. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
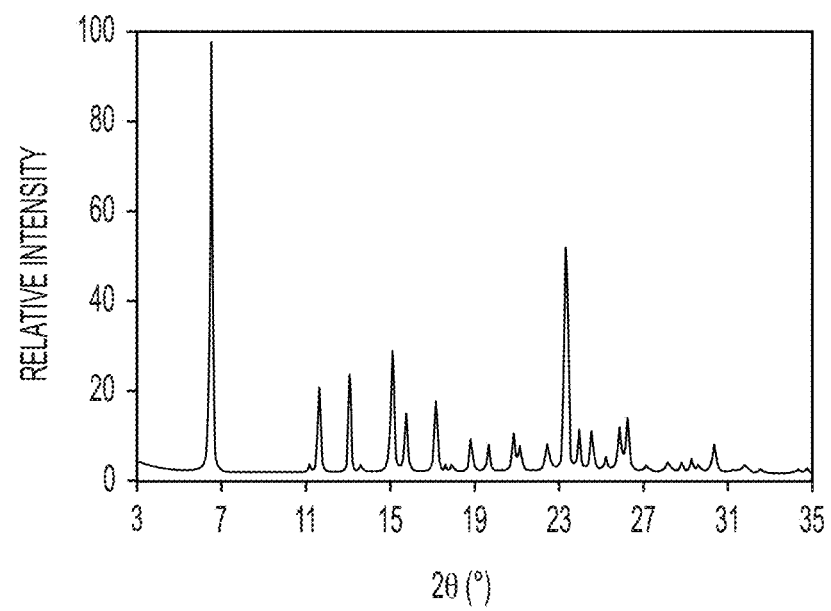
FIG. 1 shows a powder x-ray diffraction (PXRD) pattern of crystalline (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I').

In one aspect, the invention relates to crystalline (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I').

Compound I' of the invention contains two chiral centers and therefore, a compound of such a structure may exist in various stereoisomeric forms. Specifically, the carbon atoms may have a particular (R,R), (S,S), (S,R), or (R,S) configuration or are enriched in a stereoisomeric form having such configuration. Compound I', as shown and named is in the (2S,4R) configuration. It will be understood by those skilled in the art that minor amounts of the other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Compound I' of the invention possesses neprilysin (NEP) inhibition activity, that is, the compound is able to inhibit enzyme-catalytic activity. One measure of the ability of a compound to inhibit NEP activity is the inhibition constant ($pK_i$). The $pK_i$ value is the negative logarithm to base 10 of the dissociation constant ($K_i$), which is typically reported in molar units. The compound of the invention has a $pK_i$ at NEP≥9.0. Other properties and utilities of Compound I' can be demonstrated using in vitro and in vivo assays that are well-known to those skilled in the art, including, inter alia, those described in U.S. Pat. No. 9,126,956.

Compound I', as well as those compounds used in its synthesis, may also include isotopically-labeled compounds, that is, where one or more atoms have been enriched with atoms having an atomic mass different from the atomic mass predominately found in nature. Examples of isotopes that may be incorporated into the compounds described in this invention, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest is Compound I' enriched in tritium or carbon-14 which can be used, for example, in tissue distribution studies; Compound I' enriched in deuterium especially at a site of metabolism resulting, for example, in a compound having greater metabolic stability; and Compound I' enriched in a positron emitting isotope, such as $^{11}C$, $^{18}F$, $^{15}O$ and $^{13}N$, which can be used, for example, in Positron Emission Topography (PET) studies.

Chemical structures are named herein according to IUPAC conventions as implemented in ChemDraw software (Perkin Elmer, Inc., Cambridge, Mass.).

Definitions

When describing the compound, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "about" or "approximately" when used in the context of thermal behavior of Compound I' is defined as ±1-3° C. The term "approximate" when used in the context of % dose of Compound I' excreted in the urine is defined by a margin of error that is typically about twice the standard deviation or the half-width of a 95 percent confidence interval. The term "approximate" in other areas of the disclosure may be used to indicate standard deviation or the amount of variation or dispersion of a set of data values.

The term "controlled-release" as used herein is synonymous with sustained-release and extended-release and relates to amount of drug delivered over extended period of time in a subject. Generally, controlled-release tablets and capsules release the active into the subject over time periods of about 8-, 12-, 16-, and 24-hours. On the other hand, the term "immediate-release" refers to the active being released in a subject within a small period of time, typically less than about 30 minutes. The term "delayed-release" is directed to tablets and capsules that release the pharmaceutical dose after a set period of time. These dosage forms are usually enteric-coated in order to prevent release in the stomach but allow the release in the intestinal track.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

In general, in describing pharmaceutical solids, the term "non-solvated" implies "without solvent". Thus, when the crystalline form of the invention is described as being "non-solvated," it is meant that the crystalline particles essentially contain only (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid molecules; the form contains no significant amounts of other lattice-included solvent molecules or in other words, solvent is not significantly incorporated into the crystal lattice. The term "non-solvated" is synonymous with the term "non-hydrated" when water is the solvent. The term "anhydrous" means the crystal contains negligible to no water, especially water of crystallization. A negligible amount of water means the limit of detection that water can be measured. For example, measuring water content by Karl Fischer (% w/w) in this application may have a limit of quantification (LOQ) of 0.20% w/w. Therefore, the amount of water found in Compound I' would be reported as <LOQ or <0.20% w/w. Furthermore, a hygroscopic substance is one that readily attracts water from its surroundings, through either absorption or adsorption. The term "non-hygroscopic" is used to describe crystals that have little to no tendency to adsorb moisture to its surfaces or absorb water into its crystal lattice.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "subject" or "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

General Synthetic Procedures

Crystalline form of Compound I of the invention can be synthesized from readily available starting materials as described below and in the Examples. It will be appreciated that where typical or preferred process conditions (i.e., reaction temperatures, crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature means a temperature within the range commonly associated with the ambient temperature in a laboratory environment, and will typically be in the range of about 15° C. to about 30° C., such as about 20° C. to about 25° C. In other instances, reactions or crystallizations were conducted at room temperature and the temperature was actually measured and recorded.

Any molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

In one embodiment, Compound I can be prepared by (a) coupling benzyl (2S,4R)-4-amino-5-(5'-chloro-2'-fluoro-[1,1'-biphenyl]-4-yl)-2-(ethoxymethyl)-2-methylpentanoate hydrochloride with 3-((4-methoxybenzyl)oxy)isoxazole-5-carboxylic acid in a solvent in approximately a 1:1 molar ratio to give benzyl (2S,4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate; and (b) deprotecting benzyl (2S,4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate to form (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I).

In one embodiment, step (a) further includes the addition of a peptide coupling agent and a base in approximately a 1:3:1:1 molar ratio of coupling agent to base to benzyl (2S,4R)-4-amino-5-(5'-chloro-2'-fluoro-[1,1'-biphenyl]-4-yl)-2-(ethoxymethyl)-2-methylpentanoate hydrochloride to 3-((4-methoxybenzyl)oxy)isoxazole-5-carboxylic acid. Representative examples of peptide coupling agents include, but are not limited to, O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), 0-(6-Chlorobenzotriazol-1-yl)-N,N,N',N'-tetramethyluronium hexafluorophosphate (HCTU), and O-[(Ethoxycarbonyl)cyanomethylenamino]-N,N,N',N'-tetra methyluronium tetrafluoroborate (TOTU). In a preferred embodiment, the peptide coupling agent is HATU, HBTU and HCTU, with HCTU being most preferred. An example of a base that can be used in the reaction is DIPEA.

In another embodiment, the deprotecting step (b) is performed with a palladium catalyst, for example palladium on carbon (5% or 10% w/w), and hydrogen gas. In additional embodiments, the following steps may be performed after step (b). The palladium catalyst is removed, followed by addition of an oxidizing agent such as hydrogen peroxide. The reaction may then be stirred for at least 1 h or preferably 2 h at a temperature between about 20° C. and 30° C. This step may be followed by distilling and washing one or more times, and optionally cooling and aging, prior to isolation of Compound I.

In one embodiment, the invention relates to a crystalline form of (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I'). In another embodiment, the crystalline form is anhydrous, non-hygroscopic or both.

Preparation of crystalline form I' is generally conducted in a suitable inert diluent, examples of which include, but are not limited to, acetone, acetonitrile, ethyl acetate, methyl ethyl ketone, methanol, ethanol, isopropanol, isobutanol, dichloromethane, methyl t-butyl ether, cyclopentyl methyl ether, hexanes, and the like, and mixtures thereof, optionally containing water. Mixtures of inert diluents (also referred to as solvent systems) include acetone with water, acetonitrile with water, ethanol and ethyl acetate, ethyl acetate and hexanes, and lower alcohols ($C_{1-6}$alkyl-OH) with water, for example, methanol and water and isopropanol and water. Particularly suitable solvent systems include ethyl acetate and water. Upon completion of the crystallization, the crystalline compound can be isolated from the reaction mixture by any conventional means such as precipitation, filtration, concentration, centrifugation, dried in vacuo, and the like.

In one embodiment, the crystalline form I' can be prepared by (a) forming a solution comprising (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (Compound I) with a solvent, optionally containing a metal scavenger, at an elevated temperature; (b) cooling the solution to a temperature between about −20° C. to 5° C.; and (c) isolating the resulting solids to yield the crystalline form I'. In another embodiment, the process further includes stirring or agitating the solution at a temperature between about −20° C. and 5° C.

Step (a) is generally conducted at room temperature in a polar solvent. The polar solvent can be protic or aprotic and include, for example, a mixture of ethyl acetate and water, ethyl acetate, or ethanol. The elevated temperature in step (a) is typically between about 60° C. and 95° C. and preferably between 70° C. and 85° C., 70° C. and 80° C., or 75° C. and 85° C. The isolation step (c) involves filtering, washing with one or more solvents, drying in air or under vacuum, or a combination of these steps. If Compound I' or crystalline form I' is dried under vacuum, this may be done at a temperature between 25° C. and 70° C., preferably between 30° C. and 60° C., 30° C. and 50° C., 40° C. and 60° C., or 40° C. and 50° C.

In another embodiment, the process further includes the step of stirring the mixture at a temperature between 0° C. and 30° C. for at least 5 minutes prior to elevating the temperature to between about 60° C. and 95° C. Alternatively, stirring may be performed at a temperature between 25° C. and 35° C. for at least 1 h.

In a further another embodiment, the mixture is further settled and an upper non-aqueous phase is isolated prior to elevating the temperature. Alternatively, the mixture is filtered, rinsed and reduced in volume prior to elevating the temperature.

In yet another embodiment, the temperature in step (b) of the process above is independently between −15° C. and −5° C. or alternatively, independently between −5° C. and 5° C.

Crystalline Properties

As is well known in the field of powder x-ray diffraction (PXRD) analysis, relative peak heights of PXRD patterns are dependent on a number of factors relating to sample preparation and instrument geometry, while peak positions are relatively insensitive to experimental details. PXRD, differential scanning calorimetry (DSC), thermal gravimetric analyses (TGA), and dynamic moisture sorption (DMS) assessment (also known as moisture sorption-desorption analysis) were performed as described herein.

In one aspect, the invention relates to crystalline form of (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I') and characterized by a PXRD pattern in which the peak positions are substantially in accordance with those shown in FIG. 1.

Peaks with relative intensities greater than 1% in area are listed in the table below. This pattern shows sharp diffraction peaks in the range of 5-35° in 2θ. These and other peaks in the diffraction pattern can be used to identify this form.

| 2θ* | d (Å) | Area | Area % |
|---|---|---|---|
| 6.51 | 13.57 | 10871.5 | 100 |
| 11.17 | 7.92 | 199.4 | 1.8 |
| 11.62 | 7.61 | 2441.7 | 22.5 |
| 13.05 | 6.78 | 2380.2 | 21.9 |
| 15.07 | 5.88 | 3944.4 | 36.3 |
| 15.72 | 5.63 | 1321.5 | 12.2 |
| 17.12 | 5.18 | 2026.8 | 18.6 |
| 17.12 | 5.18 | 2026.8 | 18.6 |
| 18.77 | 4.72 | 979.9 | 9.0 |
| 19.63 | 4.52 | 585.3 | 5.4 |
| 20.79 | 4.27 | 1339.1 | 12.3 |
| 21.10 | 4.21 | 1192.2 | 11.0 |
| 22.38 | 3.97 | 814.6 | 7.5 |
| 23.28 | 3.82 | 6169.3 | 56.7 |
| 23.89 | 3.72 | 840.8 | 7.7 |
| 24.48 | 3.63 | 1053.9 | 9.7 |
| 25.17 | 3.54 | 281.4 | 2.6 |
| 25.81 | 3.45 | 1604.8 | 14.8 |
| 26.19 | 3.40 | 1943.7 | 17.9 |
| 27.05 | 3.29 | 181.9 | 1.7 |
| 28.11 | 3.17 | 363.1 | 3.3 |
| 28.76 | 3.10 | 176.1 | 1.6 |
| 29.21 | 3.06 | 372.8 | 3.4 |
| 30.29 | 2.95 | 1003.4 | 9.2 |
| 31.76 | 2.816 | 486.3 | 4.5 |

*2θ values are reported as value ± 0.20.

Thus, in one embodiment, crystalline form I' is characterized by PXRD pattern comprising diffraction peaks at 2θ values of 6.51±0.20, 11.62±0.20, 13.05±0.20, 15.07±0.20, and 23.28±0.20.

In another embodiment, the crystalline form I' is characterized by PXRD pattern comprising diffraction peaks at 2θ values of 6.51±0.20, 11.62±0.20, 13.05±0.20, 15.07±0.20, 17.12±0.20, 23.28±0.20, and 26.19±0.20.

In another embodiment, the crystalline form I' is further characterized by having one or more additional diffraction peaks at 2θ values selected from 6.51±0.20, 11.62±0.20, 13.05±0.20, 15.07±0.20, 15.72±0.20, 17.12±0.20, 20.79±0.20, 21.10±0.20, 23.28±0.20, 24.48±0.20, 25.81±0.20, and 26.19±0.20; and in yet another embodiment the crystalline compound is further characterized by having three or more such additional diffraction peaks.

Figure 2:
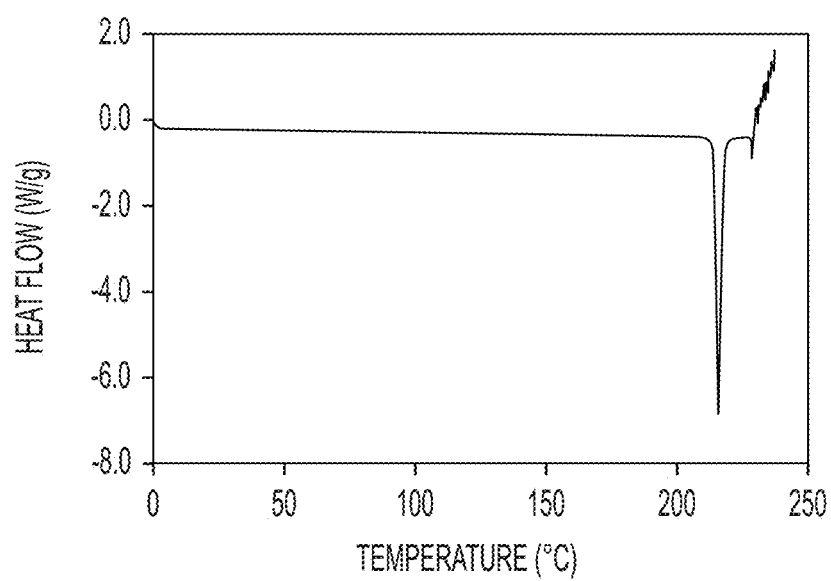
FIG. 2 shows a differential scanning calorimetry (DSC) thermogram of the crystalline form (I').

In one embodiment, crystalline form I' is characterized by the DSC thermogram or differential scanning calorimetry trace substantially in accordance with that shown in FIG. 2. The crystalline form I' is characterized by a differential scanning calorimetry trace recorded at a heating rate of 10° C. per minute which shows a maximum in endothermic heat flow at a temperature between about 214° C. and about 218° C. The DSC thermogram or differential scanning calorimetry trace illustrates a melting endotherm with a peak at about 216.1° C., onset at 214.2° C., and with an area under the endotherm corresponding to 107.2 J/g. Decomposition of the compound coincides with melting and the contribution of 107.2 J/g towards melting enthalpy is not established.

Figure 3:
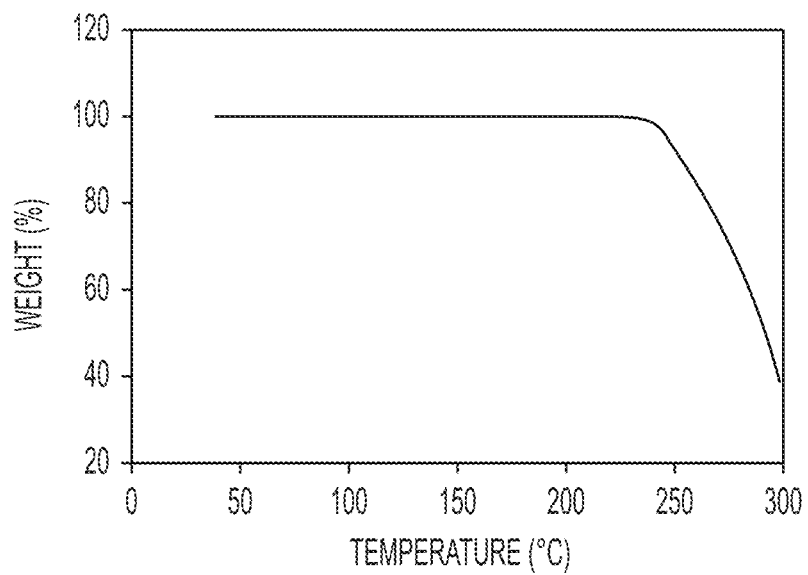
FIG. 3 shows a thermal gravimetry profile for the crystalline form (I').

In one embodiment, crystalline form I' is characterized by the TGA profile in FIG. 3. This profile shows no mass loss until about 240° C.; the crystalline compound decomposes after melting, as seen by significant weight loss occurring at an onset of approximately 242° C. There is no additional loss of mass up to the decomposition temperature, indicating a lack of adsorbed molecules such as water.

Figure 4:
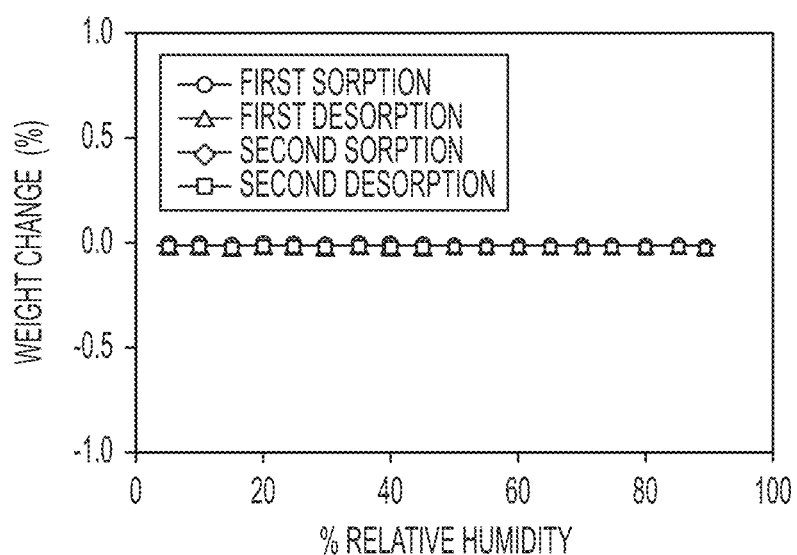
FIG. 4 shows a dynamic moisture sorption (DMS) isotherm of the crystalline form (I').

In one embodiment, crystalline form I' is characterized by the DMS isotherm in FIG. 4. This form is a non-hygroscopic solid. The total moisture gain observed is less than 0.02% by weight when exposed to 5-90% relative humidity. No significant hysteresis is found between two consecutive sorption-desorption cycles. The solid obtained after sorption-desorption cycles showed the same PXRD pattern as the starting material, indicating no change in form after this experiment. These data indicate that the crystalline form I' does not convert to a hydrated form in the presence of water. The crystalline form I' remains non-hygroscopic and therefore may be characterized as anhydrous, non-hygroscopic or both.

Figure 5:
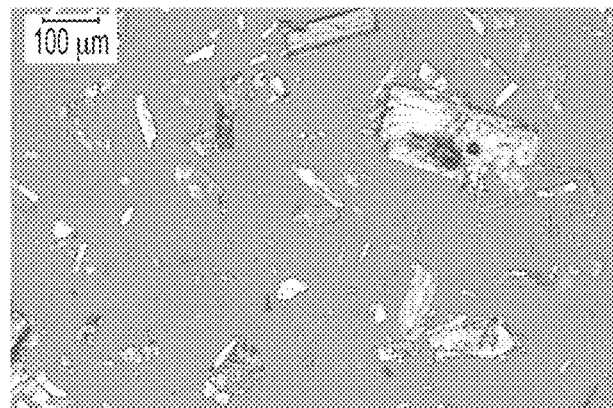
FIG. 5 is a polarized light microscope (PLM) image of the crystalline form (I').

The crystalline form I' can be characterized by the PLM image in FIG. 5, which shows this form as being crystalline, birefringent, plate-like particles.

Utility

The in vitro-to-in vivo extrapolation of drug behavior in a subject continues to improve (see, e.g., Chiba et al., *AAPS J.*, 2009 June; 11(2): 262-276). In the present invention, in vitro human neprilysin inhibitor activity was assessed in order to determine neprilysin inhibitory activity of Compound I and crystalline form I'. A threshold of $pK_i \geq 9.0$ was met. However, additional in vivo experiments were further performed in order to more accurately predict the behavior of Compound I and crystalline form I' in a subject.

Regarding in vivo behavior, there are several properties that useful in evaluating whether a sufficient amount of the drug will be delivered to the plasma in order to achieve the necessary therapeutic benefit, for example low plasma clearance across all species tested, high oral bioavailability, favorable potentiation of the cyclic guanosine monophosphate (cGMP) response and low renal clearance for those subjects with compromised kidney function.

For the present invention, oral and intravenous pharmacokinetic studies were conducted in rat, dog and monkey species in order to determine the oral bioavailability of the Compound I, i.e., the soluble form of Compound I' (Assay 1). This assay was also used to determine the rate of plasma clearance for these compounds; a low clearance rate is believed to be predictive of how long the compound is expected to remain in circulation, i.e., its in vivo stability and persistence without identifying the individual elimination processes involved.

Pharmacokinetic/pharmacodynamic studies were conducted in humans in order to determine the level of neprilysin inhibition that is obtained with Compound I (Assay 3). In this assay the level of cyclic guanosine monophosphate (cGMP) was measured. cGMP is a downstream effector molecule of natriuretic peptide receptor binding and thus serves as an effective in vivo biomarker of natriuretic peptide activity. The level of cGMP increases when an animal is administered a neprilysin inhibitor as compared to placebo. One embodiment of the invention relates to a method of increasing atrial natriuretic peptide (ANP) or cGMP basal levels in a subject with hypertension, heart failure, or renal disease comprising administering to a subject a therapeutically effective amount of the Compound I or crystalline form I'. Levels of ANP and cGMP are measured in either urine or plasma or both in a subject. In another embodiment, the level of ANP or cGMP is elevated at least ≥1.1-fold, ≥1.2-fold, ≥1.3-fold, ≥1.4-fold, ≥1.5-fold, ≥2-fold, ≥3-fold, ≥4-fold, or ≥5-fold over a 24-hour period in a subject when administered a therapeutically effective amount of Compound 1 or crystalline form I'. In another aspect, the invention relates to a method for increasing the amount of cyclic guanosine monophosphate in the plasma of a human, the method comprising administering to the human a crystalline free acid form of In one aspect, the invention relates to reducing the blood pressure in a human, the method comprising administering to the human a blood pressure-reducing amount of a crystalline free acid form of (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid.

Crystalline form I', which dissolves to its soluble form, Compound I, in a subject, inhibits the NEP enzyme, and therefore is expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of Compound I or crystalline form I'. For example, by inhibiting NEP, Compound I or crystalline form I' is expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, this compound is expected to have other physiological actions, for example, on the renal, central nervous, reproductive and gastrointestinal systems.

Drugs are removed from a subject body by various elimination processes which are categorized generally as excretion and biotransformation. Excretion relates to the removal of the intact non-volatile drug mainly by renal (kidney) to bladder to urine while other pathways of excretion include bile (liver), sweat, saliva, milk (via lactation) or other bodily fluids. Volatile drugs like alcohol and gaseous anesthetics are excreted via the lungs into expired air. On the other hand, biotransformation, or drug metabolism, relates to a drug being chemically converted in the body to a metabolite and is usually an enzymatic process. Exception to this is when a drug is chemically changed non-enzymatically, e.g., ester hydrolysis. Enzymes involved in biotransformation of drugs are located mainly in the liver. Other tissues such as kidney, lung, small intestine and skin also contain metabolic enzymes.

Pharmacokinetic studies can also be used to investigate elimination pathways in a subject, e.g., renal clearance via excretion of the administered drug in urine over time. The renal excretion of Compound I in rat, dog and monkey species as well as humans was conducted to assess kidney excretion as an elimination pathway (Assays 2 and 4). This elimination pathway is important for subjects that have compromised kidney function and need therapies that are minimally cleared by kidney excretion. In one embodiment, the renal excretion of Compound I or crystalline form I' in the subject is approximately ≤15%, ≤10%, ≤5%, ≤3%, ≤2%, ≤1% or ≤0.5% of the administered dose over 24 hours.

As described in the assay section below, in vivo determinations of plasma clearance, oral bioavailability, and renal excretion in multiple animal species were made. Compound I or crystalline form I' exhibited high inhibitory activity of human neprilysin, high oral bioavailability, low plasma clearance, increased potentiation of cGMP and low renal excretion expected to lead to particular utility in the treatment of disease.

Cardiovascular Diseases

By potentiating the effects of vasoactive peptides like the natriuretic peptides and bradykinin, Compound I and crystalline form I' are expected to find utility in treating and/or preventing medical conditions such as cardiovascular diseases. See, for example, Roques et al. (1993) *Pharmacol. Rev.* 45:87-146 and Dempsey et al. (2009) *Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension, pulmonary arterial hypertension, chronic thromboembolic pulmonary hypertension (CTEPH), or hypertension with renal artery stenosis comprising administering to a patient a therapeutically effective amount of Compound I or crystalline form I'.

For treatment of primary hypertension, the therapeutically effective amount is typically the amount that is sufficient to lower the patient's blood pressure. In one aspect, the invention relates to reducing the blood pressure in a human, the method comprising administering to the human a blood pressure-reducing amount of a crystalline free acid form of (2S,4R)-5-(5'-chloro-2'-fluoro-[1,1'-biphenyl]-4-yl)-2-

(ethoxymethyl)-4-(3-hydroxyisoxazole-5-carboxamido)-2-methylpentanoic acid. This would include treatment for both mild-to-moderate hypertension and severe hypertension. When used to treat hypertension, Compound I or crystalline form I' may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting $\beta$-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, the compound of the invention is combined with an $AT_1$ receptor antagonist, a calcium channel blocker, a diuretic, or a combination thereof, and used to treat primary hypertension. In another particular embodiment of the invention, the compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension Compound I or crystalline form I' may be administered in combination with other therapeutic agents such as α-adrenergic receptor antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, Compound I or crystalline form I' is combined with a PDE-V inhibitor or a selective serotonin reuptake inhibitor and used to treat pulmonary arterial hypertension.

For treatment of chronic thromboembolic pulmonary hypertension, the therapeutically effective amount is typically the amount that is sufficient to reduce blood pressure in the pulmonary arteries whether or not a pulmonary embolism has formed in a subject.

Additionally, for treatment of hypertension with renal artery stenosis, the therapeutically effective amount is typically the amount that is sufficient to lower blood pressure. For subjects that have renal artery stenosis, the arteries are narrowed due to atherosclerosis. This in turn causes the body to register less blood reaching the kidneys, interpreting this as low blood pressure, which in turn signals a release of hormones to increase blood pressure. Over time this can lead to kidney failure.

Another embodiment of the invention relates to a method for treating heart failure, in particular congestive heart failure (including both systolic and diastolic congestive heart failure), comprising administering to a patient a therapeutically effective amount of Compound I or crystalline form I'. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, Compound I or crystalline form I' may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting $\beta$-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, Compound I or crystalline form I' is combined with an aldosterone antagonist, a $\beta_1$-adrenergic receptor antagonist, an $AT_1$ receptor antagonist, or a diuretic, and used to treat congestive heart failure.

Diarrhea

As a NEP inhibitor, Compound I or crystalline form I' is expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Margais-Collado (1987) *Eur. J. Pharmacol.* 144(2): 125-132. When used to treat diarrhea, Compound I or crystalline form I' may be combined with one or more additional antidiarrheal agents.

Renal Diseases

By potentiating the effects of vasoactive peptides like the natriuretic peptides and bradykinin, Compound I or crystalline form I' is expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases in a renally-impaired subject. Renal diseases of particular interest include diabetic nephropathy, chronic kidney disease, proteinuria, and particularly acute kidney injury (caused, for example, by cardiovascular surgery, chemotherapy, or the use of contrast dyes in medical imaging) or acute renal failure (see Sharkovska et al. (2011) *Clin. Lab.* 57:507-515 and Newaz et al. (2010) *Renal Failure* 32:384-390). Other renal diseases of particular interest include nephrotic syndrome, focal segmental glomerulosclerosis (FSGS) and polycystic kidney disease (PKD).

A renally-impaired subject that has chronic kidney disease (CKD) may be classified according to the National Kidney Foundation Kidney Disease Outcomes Quality Initiative (NKF KDOQI) Guidelines. Once chronic kidney disease is established, i.e., kidney damage or glomerular filtration rate (GFR) <60 mL/min/1.73 m² for ≥3 months, the stage of disease may be assigned according to KDOQI CKD classification. These include Stage 1 (kidney damage with normal or increased GFR): GFR ≥90; Stage 2 (kidney damage with mild decreased GFR): GFR 60-89; Stage 3 (Moderate decreased GFR): GFR 30-59; Stage 4 (severe decrease GFR): GFR 15-29; and Stage 5 (kidney failure): GFR <15 (or dialysis). GFR is defined in units of mL/min/1.73 m².

One embodiment includes a method of treating a renally-impaired subject comprising administering a therapeutically effective amount of Compound I or crystalline form I'. This method further includes treating a renally-impaired subject with hypertension or heart failure. When used to treat renal disease, Compound I or crystalline form I' may be administered in combination with other therapeutic agents such as angiotensin-converting enzyme inhibitors, $AT_1$ receptor antagonists, and diuretics.

Another embodiment includes a method of treating a renally-impaired subject having chronic kidney disease with an estimated glomerular filtration rate (eGFR) between 60 mL/min/1.73 m² and 15 mL/min/1.73 m² comprising administering to a patient a therapeutically effective amount of Compound I or crystalline form I'. Another embodiment includes a method of treating a renally-impaired subject having chronic kidney disease with an estimated glomerular filtration rate (eGFR) ≥90 mL/min/1.73 m² (Stage 1) or an eGFR <15 mL/min/1.73 m² (Stage 5) comprising administering to a patient a therapeutically effective amount of Compound I or crystalline form I'. For purposes of this invention, severe kidney disease may be classified as an eGFR <30 mL/min/1.73 m². In yet another embodiment, a method of treating a renally-impaired subject having chronic kidney disease classified as Stage 1, Stage 2, Stage 3, Stage 4, Stage 5 or eGFR ranges covering one or more of these stages Compound I or crystalline form I' is included.

Preventative Therapy By potentiating the effects of the natriuretic peptides, Compound 1 is also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, Compound I or crystalline form I' is expected to be useful to treat glaucoma. See, for example, Diestelhorst et al. (1989) *International Ophthalmology* 12:99-101. When used to treat glaucoma, Compound 1 may be combined with one or more additional antiglaucoma agents.

Pain Relief

As a NEP inhibitor, Compound I or crystalline form I' is expected to inhibit the degradation of endogenous enkephalins and thus such compound may also find utility as an analgesic. See, for example, Roques et al. (1980) *Nature* 288:286-288 and Thanawala et al. (2008) *Current Drug Targets* 9:887-894. When used to treat pain, Compound I or crystalline form I' may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-$HT_{1D}$ serotonin receptor agonists, and tricyclic antidepressants.

Other Utilities

Due to its NEP inhibition properties, Compound I or crystalline form I' is also expected to be useful as an antitussive agent, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, Compound I or crystalline form I' is expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, the compound of the invention may be combined with one or more of the following secondary agents: PDE-V inhibitors, dopamine agonists, estrogen receptor agonists and/or antagonists, androgens, and estrogens. Due to its NEP inhibition property, Compound I or crystalline form I' is also expected to have anti-inflammatory properties, and is expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to its NEP inhibition property, Compound I or crystalline form I' is also expected to be useful in providing protection from nerve impairment caused by diabetes or diet induced obesity.

The amount of Compound I or crystalline form I' administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of Compound I or crystalline form I' will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Compound I also finds utility as an intermediate useful for the preparation of crystalline forms of Compound I, including, for example, crystalline form I'

Research Tools

Since Compound I or crystalline form I' possesses NEP enzyme inhibition activity, it is also useful as a research tool for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of Compound I or crystalline form I'.

When used as a research tool, a biological system or sample comprising a NEP enzyme is typically contacted with a NEP enzyme-inhibiting amount of Compound I or crystalline form I'. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, Compound I or crystalline form I' can be used as a research tool for evaluating other chemical compounds, and thus is also useful in screening assays to discover, for example, new compounds having NEP-inhibiting activity. In this manner, Compound I or crystalline form I' is used as a standard in an assay to allow comparison of the results obtained with a test compound and with Compound I or crystalline form I' to identify those test compounds that have about equal or superior activity, if any. For example, $pK_i$ data for a test compound or a group of test compounds is compared to the $pK_i$ data for Compound I or crystalline form I' to identify those test compounds that have the desired properties, for example, test compounds having a $pK_i$ value equal or superior to the compound of the invention. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with Compound I or crystalline form I' to provide a second assay value; wherein step (a) is conducted either before, after or concurrently with step (b); and (c) comparing the first assay value from step (a) with the second assay value from step (b). Exemplary biological assays include a NEP enzyme inhibition assay.

Still another aspect of the invention relates to a method of studying a biological system or sample comprising a NEP enzyme, the method comprising: (a) contacting the biological system or sample with Compound I or crystalline form I'; and (b) determining the effects caused by the compound on the biological system or sample.

Pharmaceutical Compositions and Formulations

Compound I or crystalline form I' is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, Compound I or crystalline form I' may be administered, for example orally, in multiple doses per day (for example, two, three, or four times daily), in a single daily dose or a single weekly dose. It will be understood that any form of Compound I or crystalline form I', (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and Compound 1. The composition may contain other therapeutic and/or formulating agents if desired. When discussing compositions, "Compound I or crystalline form I'" may also be referred to herein as the "active agent," to distinguish it from other components of the formulation, such as the carrier. Thus, it is understood that the term "active agent" includes Compound I or crystalline form I' as well as its pharmaceutically acceptable salts.

The pharmaceutical compositions of the invention typically contain a therapeutically effective amount of Compound I or crystalline form I'. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-99 wt % of active agent, with the actual amount depending upon the formulation itself, the route of administration, the frequency of dosing, and so forth. In one embodiment, a composition suitable for an oral dosage form, for example, may contain about 10-99 wt %, or from about 50-99 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; fatty acid salts, such as magnesium stearate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

In one embodiment of the invention, the pharmaceutically acceptable carrier is magnesium stearate. For example, the pharmaceutical composition may comprise Compound I or crystalline form I' and magnesium stearate in a ratio of about 3:1 to about 10:1 of Compound I or crystalline form I' to magnesium stearate. Other ratios of Compound I or crystalline form I' to magnesium stearate include, but are not limited to, 1:1, 5:1, 15:1, 20:1, 25:1, 30:1 and 50:1. In another embodiment, the amount of Compound I or crystalline form I' to magnesium stearate may be expressed as a weight %. For example, a pharmaceutical composition may comprise 99 wt % of Compound I or crystalline form I' and 1 wt % of magnesium stearate. In another embodiment, the weight ratio of Compound I or crystalline form I' to magnesium stearate is between 85:15 and 99:1, respectively. In a preferred embodiment, the weight ratio of Compound I or crystalline form I' to magnesium stearate is between 95:5 and 99:1, preferably 99:1.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate, dicalcium phosphate, or magnesium stearate. Solid dosage forms may also comprise fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents. For the purpose of this invention, the terms "pharmaceutically acceptable carriers" are inclusive of all the terms such as carriers, fillers or extenders, binders, humectants, solution retarding agents, wetting agents, absorbents, lubricants, coloring agents and buffering agents described above.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

One embodiment of the invention includes an oral dosage form comprising Compound I or crystalline form I' in a capsule, tablet, liquid or suspension. Another embodiment of the invention relates to an oral dosage form where a release of the Compound I or crystalline form I' in a subject is an immediate, controlled or delayed release. If a capsule is used as an oral dosage form, another embodiment includes the capsule being comprised of gelatin, polysaccharides or synthetic polymers. In a particular embodiment, the capsule comprises hydroxypropyl methylcellulose.

Suitable capsule materials according to the invention are selected from gelatin, cellulose derivatives, starch, starch derivatives, chitosan and synthetic plastics. If gelatin is used as the capsule material, it may be used in admixture with other additives selected from polyethylene glycol (PEG), glycerol, sorbitol, polypropylene glycol, PEO-PPO block copolymers and other polyalcohols and polyethers. When a cellulose derivative is used as the capsule material, hydroxypropylmethylcellulose, hydroxypropylcellulose, methylcellulose, hydroxymethylcellulose and hydroxyethylcellulose are preferred polymers. If synthetic plastics are used as a capsule material, polyethylene, polycarbonate, polyester, polypropylene and polyethylene terephthalate are preferred materials. Particularly preferred are polyethylene, polycarbonate or polyethylene terephthalate.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compound I or crystalline form I' and compositions thereof can also be administered parenterally, for example, by subcutaneous, intravenous, intramuscular, or intraperitoneal injection. For such administration, the active agent is provided in a sterile solution, suspension, or emulsion. Exemplary solvents for preparing such formulations include water, saline, electrolytes, low molecular weight alcohols such as propylene glycol and polyethylene glycol, oils, amino acids, gelatin, sugars, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages that may be present in the compound. These formulations may be rendered sterile by use of a sterile injectable medium, a sterilizing agent, filtration, irradiation, or heat.

Representative physiologically-acceptable aqueous carriers include, by way of example, Sterile Water for Injection, USP; Dextrose Injection, USP (e.g., 2.5, 5.0, 10, 20% dextrose, including 5% Dextrose Injection (D5/W)); Dextrose and Sodium Chloride Injection, USP (e.g., dextrose varying from 2.5 to 10% and sodium chloride varying from 0.12 (19 mEq sodium) to 0.9% (154 mEq sodium)); Mannitol Injection, USP, (e.g., 5, 10, 15, 20 and 25% mannitol); Ringer's Injection, USP (e.g., 147 mEq sodium, 4 mEq potassium, 4.5 mEq calcium and 156 mEq chloride per liter); Lactated Ringer's Injection, USP (e.g., 2.7 mEq calcium, 4 mEq potassium, 130 mEq sodium, and 28 mEq lactate per liter); Sodium Chloride Injection, USP (e.g., 0.9% sodium chloride) and the like.

When administered to a patient, Compound I or crystalline form I' will typically be diluted in about 0.5 mL to about 10 mL of the aqueous carrier per mg of the Compound I or crystalline form I', such as about 0.6 to about 8 mL per mg.

In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin.

Exemplary buffers for such formulations include carboxylic acid-based buffers such as citrate, lactate and maleate buffer solutions. In one embodiment of the invention, an intravenous dosage form comprises Compound I or crystalline form I' in a buffered solution.

In one embodiment, Compound I or crystalline form I' or a pharmaceutical composition thereof is a lyophilized powder. Typically, the lyophilized powder is sterile and is packaged in a hermetically-sealed vial or ampoule or similar container.

Compound I or crystalline form I' can also be administered transdermally using known transdermal delivery systems and excipients. For example, Compound I or crystalline form I' can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

Compound I or crystalline form I' may be useful as the sole treatment of a disease or may be combined with one or more additional therapeutic agents in order to obtain the desired therapeutic effect. Thus, in one embodiment, pharmaceutical compositions of the invention contain other drugs that are co-administered with Compound I or crystalline form I'. For example, the composition may further comprise one or more drugs (also referred to as "secondary agents(s)"). Such therapeutic agents are well known in the art, and include adenosine receptor antagonists, α-adrenergic receptor antagonists, $β_1$-adrenergic receptor antagonists, $β_2$-adrenergic receptor agonists, dual-acting β-adrenergic receptor antagonist/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, antidiabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, mineralocorticoid-receptor antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors (e.g., PDE5 and PDE9), prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

A specific embodiment includes a pharmaceutical composition comprising Compound I or crystalline form I' or crystalline form thereof and an $AT_1$ receptor antagonist, an angiotensin-converting enzyme inhibitor, a phosphodiesterase (PDE) inhibitor, a renin inhibitor, a diuretic, or combinations thereof, and optionally one or more pharmaceutically acceptable carriers.

Accordingly, in yet another aspect of the invention, a pharmaceutical composition comprises Compound I or crystalline form I', a second active agent, and a pharmaceutically acceptable carrier. Third, fourth etc. active agents may also be included in the composition. In combination therapy, the amount of Compound I or crystalline form I' that is administered, as well as the amount of secondary agents, may be less than the amount typically administered in monotherapy.

Compound I or crystalline form I' may be physically mixed with the second active agent to form a composition containing both agents; or each agent may be present in separate and distinct compositions which are administered to the patient simultaneously or at separate times. For example, Compound I or crystalline form I' can be combined with a second active agent using conventional procedures and equipment to form a combination of active agents comprising Compound I or crystalline form I' and a second active agent. Additionally, the active agents may be combined with a pharmaceutically acceptable carrier to form a pharmaceutical composition comprising Compound I or crystalline form I', a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of Compound I or crystalline form I', ranging anywhere from concurrent with administration of the compound of the invention to about 24 hours post-dose. This is also referred to as sequential administration. Thus, Compound I or crystalline form I' can be orally administered simultaneously or sequentially with another active agent using two tablets, with one tablet for each active agent, where sequential may mean being administered immediately after administration of Compound I or crystalline form I' or at some predetermined time later (for example, one hour later or three hours later). It is also contemplated that the secondary agent may be administered more than 24 hours after administration of Compound I or crystalline form I'. Alternatively, the combination may be administered by different routes of administration, that is, one orally and the other by inhalation.

In one embodiment, the kit comprises a first dosage form comprising Compound I or crystalline form I' and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with Compound I or crystalline form I' of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, Compound I or crystalline form I' is administered in combination with an adenosine receptor antagonist, examples of which include naxifylline, rolofylline, SLV-320, theophylline, and tonapofylline.

In one embodiment, Compound I or crystalline form I' is administered in combination with an α-adrenergic receptor antagonist, examples of which include doxazosin, prazosin, tamsulosin, and terazosin.

Compound I or crystalline form I' may also be administered in combination with a $\beta_1$-adrenergic receptor antagonist ("$\beta_1$-blocker"), examples of which include acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, Compound I or crystalline form I' is administered in combination with a $\beta_2$-adrenergic receptor agonist, examples of which include albuterol, bitolterol, fenoterol, formoterol, indacaterol, isoetharine, levalbuterol, metaproterenol, pirbuterol, salbutamol, salmefamol, salmeterol, terbutaline, vilanterol, and the like. Typically, the $\beta_2$-adrenergic receptor agonist will be administered in an amount sufficient to provide from about 0.05-500 μg per dose.

In one embodiment, Compound I or crystalline form I' is administered in combination with an advanced glycation end product (AGE) breaker, examples of which include alagebrium (or ALT-711) and TRC4149.

In another embodiment, Compound I or crystalline form I' is administered in combination with an aldosterone antagonist, examples of which include eplerenone, spironolactone, and combinations thereof. Typically, the aldosterone antagonist will be administered in an amount sufficient to provide from about 5-300 mg per day.

In one embodiment, Compound I or crystalline form I' is administered in combination with an aminopeptidase N or dipeptidyl peptidase III inhibitor, examples of which include bestatin and PC18 (2-amino-4-methylsulfonyl butane thiol, methionine thiol).

Compound I or crystalline form I' can also be administered in combination with an angiotensin-converting enzyme (ACE) inhibitor, examples of which include accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day.

In another embodiment, Compound I or crystalline form I' is administered in combination with a dual-acting angiotensin-converting enzyme/neprilysin (ACE/NEP) inhibitor, examples of which include: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentyl-carbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4a,7a(R*),12bf]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, Compound I or crystalline form I' is administered in combination with an angiotensin-converting enzyme 2 (ACE2) activator or stimulator.

In one embodiment, Compound I or crystalline form I' is administered in combination with an angiotensin-II vaccine, examples of which include ATR12181 and CYT006-AngQb.

In one embodiment, Compound I or crystalline form I' is administered in combination with an anticoagulant, examples of which include: coumarins such as warfarin; heparin; and direct thrombin inhibitors such as argatroban, bivalirudin, dabigatran, and lepirudin.

In yet another embodiment, Compound I or crystalline form I' is administered in combination with an anti-diabetic agent, examples of which include injectable drugs as well as orally effective drugs, and combinations thereof. Examples of injectable drugs include insulin and insulin derivatives. Examples of orally effective drugs include: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, Compound I or crystalline form I' is administered in combination with antidiarrheal treatments. Representative treatment options include oral rehydration solutions (ORS), loperamide, diphenoxylate, and bismuth subsalicylate.

In yet another embodiment, Compound I or crystalline form I' is administered in combination with an anti-glaucoma agent, examples of which include: α-adrenergic agonists such as brimonidine; $\beta_1$-adrenergic receptor antagonists; topical $\beta_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, Compound I or crystalline form I' is administered in combination with an anti-lipid agent, examples of which include: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, Compound I or crystalline form I' is administered in combination with an anti-thrombotic agent, examples of which include: aspirin; anti-platelet agents such as clopidogrel, prasugrel, and ticlopidine; heparin, and combinations thereof.

In one embodiment, Compound I or crystalline form I' is administered in combination with an $AT_1$ receptor antagonist, also known as angiotensin II type 1 receptor blockers (ARBs). Representative ARBs include abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compound I or crystalline form I' may also be administered in combination with a dual-acting agent, such as an $AT_1$ receptor antagonist/neprilysin inhibitor (ARB/NEP) inhibitor, examples of which include compounds described in U.S. Pat. Nos. 7,879,896 and 8,013,005, both to Allegretti et al., such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compound I or crystalline form I' may also be administered in combination with multifunctional angiotensin receptor blockers as described in Kurtz & Klein (2009) *Hypertension Research* 32:826-834.

In one embodiment, Compound I or crystalline form I' is administered in combination with a bradykinin receptor antagonist, for example, icatibant (HOE-140). It is expected that this combination therapy may present the advantage of preventing angioedema or other unwanted consequences of elevated bradykinin levels.

In one embodiment, Compound I or crystalline form I' is administered in combination with a calcium channel blocker, examples of which include amlodipine, anipamil, aranipine, bamidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, Compound I or crystalline form I' is administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, Compound I or crystalline form I' is administered in combination with a diuretic, examples of which include: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, clothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compound I or crystalline form I' may also be administered in combination with an endothelin converting enzyme (ECE) inhibitor, examples of which include phosphoramidon, CGS 26303, and combinations thereof.

In a particular embodiment, Compound I or crystalline form I' is administered in combination with an endothelin receptor antagonist, examples of which include: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, and tezosentan.

In yet another embodiment, Compound I or crystalline form I' is administered in combination with one or more HMG-CoA reductase inhibitors, which are also known as statins. Representative statins include atorvastatin, fluvastatin, lovastatin, pitavastatin, pravastatin, rosuvastatin and simvastatin.

In one embodiment, Compound I or crystalline form I' is administered in combination with a monoamine reuptake inhibitor, examples of which include norepinephrine reuptake inhibitors such as atomoxetine, buproprion and the buproprion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, Compound I or crystalline form I' is administered in combination with a muscle relaxant, examples of which include: carisoprodol, chlorzoxazone, cyclobenzaprine, diflunisal, metaxalone, methocarbamol, and combinations thereof.

In one embodiment, Compound I or crystalline form I' is administered in combination with a natriuretic peptide or analog, examples of which include: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, Compound I or crystalline form I' is administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, Compound I or crystalline form I' is administered in combination with a neprilysin (NEP) inhibitor, examples of which include: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-(3-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, Compound I or crystalline form I' is administered in combination with a nitric oxide donor, examples of which include: nicorandil; organic nitrates such as pentaerythritol tetranitrate; and sydnonimines such as linsidomine and molsidomine.

In yet another embodiment, Compound I or crystalline form I' is administered in combination with a non-steroidal anti-inflammatory agent (NSAID), examples of which include: acemetacin, acetyl salicylic acid, alclofenac, alminoprofen, amfenac, amiprilose, aloxiprin, aniirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lomoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, Compound I or crystalline form I' is administered in combination with an N-methyl d-aspartate (NMDA) receptor antagonist, examples of which include amantadine, dextromethorphan, dextropropoxyphene, ketamine, ketobemidone, memantine, methadone, and so forth.

In still another embodiment, Compound I or crystalline form I' is administered in combination with an opioid receptor agonist (also referred to as opioid analgesics). Representative opioid receptor agonists include: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, Compound I or crystalline form I' is administered in combination with a phosphodiesterase (PDE) inhibitor, particularly a PDE-V inhibitor. Representative PDE-V inhibitors include avanafil, lodenafil, mirodenafil, sildenafil (Revatio®), tadalafil (Adcirca®), vardenafil (Levitra®), and udenafil.

In another embodiment, Compound I or crystalline form I' is administered in combination with a prostaglandin analog (also referred to as prostanoids or prostacyclin analogs). Representative prostaglandin analogs include beraprost sodium, bimatoprost, epoprostenol, iloprost, latanoprost, tafluprost, travoprost, and treprostinil, with bimatoprost, latanoprost, and tafluprost being of particular interest.

In yet another embodiment, Compound I or crystalline form I' is administered in combination with a prostaglandin receptor agonist, examples of which include bimatoprost, latanoprost, travoprost, and so forth.

Compound I or crystalline form I' may also be administered in combination with a renin inhibitor, examples of which include aliskiren, enalkiren, remikiren, and combinations thereof.

In another embodiment, Compound I or crystalline form I' is administered in combination with a selective serotonin reuptake inhibitor (SSRI), examples of which include: citalopram and the citalopram metabolite desmethyl-citalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, Compound I or crystalline form I' is administered in combination with a 5-HT$_{1D}$ serotonin receptor agonist, examples of which include, triptans such as almotriptan, avitriptan, eletriptan, frovatriptan, naratriptan, rizatriptan, sumatriptan, and zolmitriptan.

In one embodiment, Compound I or crystalline form I' is administered in combination with a sodium channel blocker, examples of which include carbamazepine, fosphenytoin, lamotrigine, lidocaine, mexiletine, oxcarbazepine, phenytoin, and combinations thereof.

In one embodiment, Compound I or crystalline form I' is administered in combination with a soluble guanylate cyclase stimulator or activator, examples of which include ataciguat, riociguat, and combinations thereof.

In one embodiment, Compound I or crystalline form I' is administered in combination with a tricyclic antidepressant (TCA), examples of which include amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, Compound I or crystalline form I' is administered in combination with a vasopressin receptor antagonist, examples of which include conivaptan and tolvaptan.

Combined secondary therapeutic agents may also be helpful in further combination therapy with the compound of the invention. For example, the compound of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with Compound I. Other therapeutic agents such as α$_2$-adrenergic receptor agonists and vasopressin receptor antagonists may also be helpful in combination therapy. Exemplary α$_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

The compound of the invention (50 g), 440 g spray-dried lactose and 10 g magnesium stearate are thoroughly blended. The resulting composition is then loaded into hard gelatin capsules (500 mg of composition per capsule). Alternately, Compound I or crystalline form I' (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, Compound I or crystalline form I' (30 g), a secondary agent (20 g), 440 g spray-dried lactose and 10 g magnesium stearate are thoroughly blended, and processed as described above.

Exemplary Gelatin Capsule Formulation for Oral Administration

Compound I or crystalline form I' (100 mg) is thoroughly blended with polyoxyethylene sorbitan monooleate (50 mg) and starch powder (250 mg). The mixture is then loaded into a gelatin capsule (400 mg of composition per capsule). Alternately, Compound 1 (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, Compound I or crystalline form I' (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Hydroxypropyl Methylcellulose (HPMC) Capsule for Oral Administration

Compound I or crystalline form I' (50 mg or 100 mg) is loaded directly into a HPMC capsule.

Exemplary Tablet Formulation for Oral Administration

Compound I or crystalline form I' (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, Compound I or crystalline form I' (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, Compound I or crystalline form I' (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, Compound I or crystalline form I' (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of Compound I or crystalline form I' per 10 mL of suspension:

| Ingredients | Amount |
| --- | --- |
| Compound I or crystalline form I' | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, Compound I or crystalline form I' (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% NaHCO$_3$ solution, with or without cyclodextrin.

Exemplary Parenteral IV Formulation for Administration by Injection

Compound I or crystalline form I' (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

The following formulations illustrate representative pharmaceutical compositions of the present invention.

Formulation Example A

A frozen solution suitable for preparing an injectable solution is prepared as follows:

| Ingredients | Amount |
| --- | --- |
| Active Compound I or I' | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active Compound I or I' is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example B

A lyophilized powder or crystalline solid suitable for preparing an injectable solution is prepared as follows:

| Ingredients | Amount |
| --- | --- |
| Active Compound I or I' | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active Compound I or I' is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

Formulation Example C

An injectable solution for intravenous administration to a patient is prepared from Formulation Example B above as follows:

Representative Procedure: The lyophilized powder of Formulation Example B (e.g., containing 10 to 1000 mg of active Compound I or I') is reconstituted with 20 mL of sterile water and the resulting solution is further diluted with 80 mL of sterile saline in a 100 mL infusion bag. The diluted solution is then administered to the patient intravenously over 30 to 120 minutes.

Exemplary Compositions for Administration by Inhalation

Compound I or I' (0.2 mg) is micronized and then blended with lactose (25 mg). This blended mixture is then loaded into a gelatin inhalation cartridge. The contents of the cartridge are administered using a dry powder inhaler, for example.

Alternately, micronized Compound I or I' (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, Compound I or I' (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of Compound I or I' per dose.

EXAMPLES

The following Reaction Schemes/Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

ACN=acetonitrile
CPME=cyclopentyl methyl ether
d=day(s)
DCC=N,N'-dicyclohexylcarbodiimide
DCM=dichloromethane or methylene chloride
DIPE=diisopropyl ether
DIPEA=N,N-diisopropylethylamine
DMF=N,N-dimethylformamide
EDTA=ethylenediaminetetraacetic acid
EtOH=ethanol
EtOAc=ethyl acetate
g=gram(s)
h=hour(s)
$H_2$=hydrogen gas
$H_2O_2$=hydrogen peroxide
HCTU=2-(6-chloro-1H-benzo[d][1,2,3]triazol-1-yl)-1,1,3,3-tetramethyluronium hexafluorophosphate(V)
HATU=N,N,N',N'-tetramethyl-O-(7-azabenzotriazol-1-yl)uronium hexafluorophosphate
HCl=hydrogen chloride
$NaBH_4$=sodium borohydride
NaCl=sodium chloride
$NaHCO_3$=sodium bicarbonate
$Na_2CO_3$=sodium carbonate
NaHMDS=sodium bis(trimethylsilyl)amide or sodium hexamethyldisilazide
NaOH=sodium hydroxide
$Na_2SO_4$=sodium sulfate
$NH_4Cl$=ammonium chloride
NMM=n-methylmorpholine
MeI=methyl iodide
MeOH=methanol
min=minute(s)
$MgSO_4$=magnesium sulfate
$Pd(PPh_3)_4$=tetrakis(triphenylphosphine)palladium(0)
Pd/C=palladium on activated carbon, 10% loading
PE=petroleum ether
$SiO_2$=silicon dioxide or silica
TFA=trifluoroacetic acid
THF=tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions was monitored by thin layer chromatography (TLC), analytical high performance liquid chromatography (anal. HPLC), and mass spectrometry, the details of which are given in specific examples. Representative analytical HPLC conditions were as follows:

| A. Analytical HPLC Conditions - Method A | |
|---|---|
| Instrument | Agilent 1260 HPLC |
| Column | Advance Material Technology HALO ®; 150 × 4.60 mm; 2.7 micron |
| Column Temperature | 30° C. |
| Flow Rate | 1.0 mL/min |
| Injection Volume | 5 μL |
| Sample Preparation | Dissolve in 1:1 ACN:water |
| Mobile Phases | A = Water:ACN:TFA (98:2:0.1) |
| | B = Water:ACN:TFA (30:70:0.1) |
| Detector Wavelength | 254 nm |
| Gradient | 22 min total |
| | Time (min)/% B: 0/30, 15/100, 18/100, 20/30, 22/30 |

| B. Analytical HPLC Conditions - Method B | |
|---|---|
| Instrument | Agilent 1260 HPLC |
| Column | Agilent Zorbax-Bonus RP-C18; 150 × 4.6 mm; 3.5 micron |
| Column Temperature | 40° C. |
| Flow Rate | 1.5 mL/min |
| Injection Volume | 5 μL |
| Sample Preparation | Dissolve in 1:1 ACN:1 M HCl |
| Mobile Phases | A = Water:TFA (99.95:0.05) |
| | B = ACN:TFA (99.95:0.05) |
| Detector Wavelength | 254 nm and 214 nm |
| Gradient | 26 min total |
| | Time (min)/% B: 0/5, 18/90, 22/90, 22.5/90, 26/5 |

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers was done by Nuclear Overhauser effect spectroscopy (NOE). Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Measurement Techniques

Powder X-Ray Diffraction

Powder X-ray diffraction analysis was performed using a Bruker D8-Advance X-ray diffractometer. The X-ray source was Cu-Kα radiation with output voltage of 40 kV and current of 40 mA. The instrument was operated in Bragg-Brentano geometry and used Goebel Mirrors to obtain parallel X-ray beam. Any divergence in the beam was limited by a 0.2° vertical divergence slit at the source and Soller slits (2.50) at the source and the detector. For measurement, a small amount of powder (5-25 mg) was gently pressed onto a zero-background silicon sample-holder to form a smooth surface and subjected to X-ray exposure. The samples were scanned in coupled θ-2θ mode from 2° to 350 in 2θ with a step size of 0.02° and a scan speed of 0.3 seconds per step. The data acquisition was controlled by Bruker DiffracSuite software and analyzed by Jade software (version 7.5.1). The instrument was calibrated with a corundum standard, within +0.02° 2θ angle.

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Differential Scanning Calorimetry

DSC measurements were performed using a TA Instruments Model Q-100 module with a Thermal Analyst controller. Data were collected and analyzed using TA Instruments Universal Analysis software. A sample was accurately weighed into a covered aluminum pan. After a 5 minute isothermal equilibration period at 5° C., the sample was heated using a linear heating ramp of 10° C./min from 0° C. to 250° C.

Thermogravimetric Analysis

Thermal gravimetry measurements were performed using a TA Instruments Model Q-500 module equipped with high resolution capability. Data were collected using TA Instruments Thermal Analyst controller and analyzed using TA Instruments Universal Analysis software. A weighed sample was placed onto a platinum pan and scanned with a heating rate of 10° C./min from ambient temperature to 300° C. The balance and furnace chambers were purged with nitrogen flow during use.

Polarized Light Microscopy

For polarized light microscope (PLM) studies, samples were examined under an optical microscope (Olympus BX51) with cross-polarized light filter. Images were collected with a PaxCam camera controlled by PaxIt Imaging Software (version 6.4). Samples were prepared on glass slides with light mineral oil as immersion medium. Depending on the size of the particles, a 4×, a 10× or a 20× objective lens was used for magnification.

Dynamic Moisture Sorption Assessment

DMS measurements were performed using a VTI atmospheric microbalance, SGA-100 system (VTI Corp., Hialeah, Fla. 33016). A weighed sample was used and the humidity was lowest possible value (close to 0% relative humidity) at the start of the analysis. The DMS analysis consisted of a scan rate of 5% relative humidity/step over the full humidity range of 5-90%. The DMS run was performed isothermally at 25° C.

Synthetic Reaction Schemes (3S,5R)-5-[[4-(5-chloro-2-fluorophenyl)phenyl]methyl]-3-(hydroxymethyl)-3-methylpyrrolidin-2-one (A) employed in this invention can be prepared from starting materials and reagents using the procedures described in Example 1 and as shown in
Scheme A:

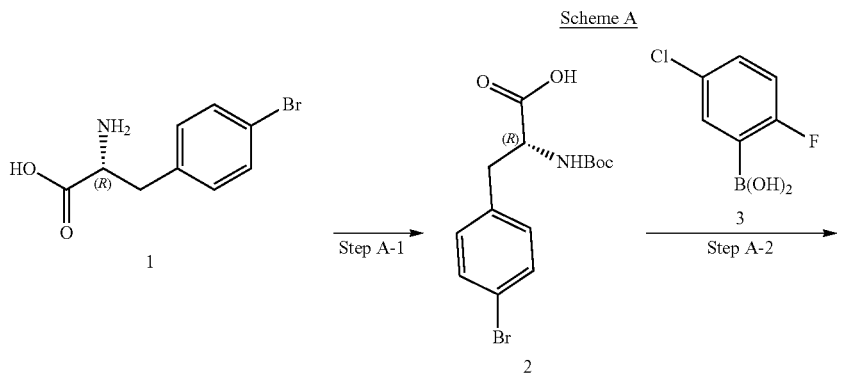

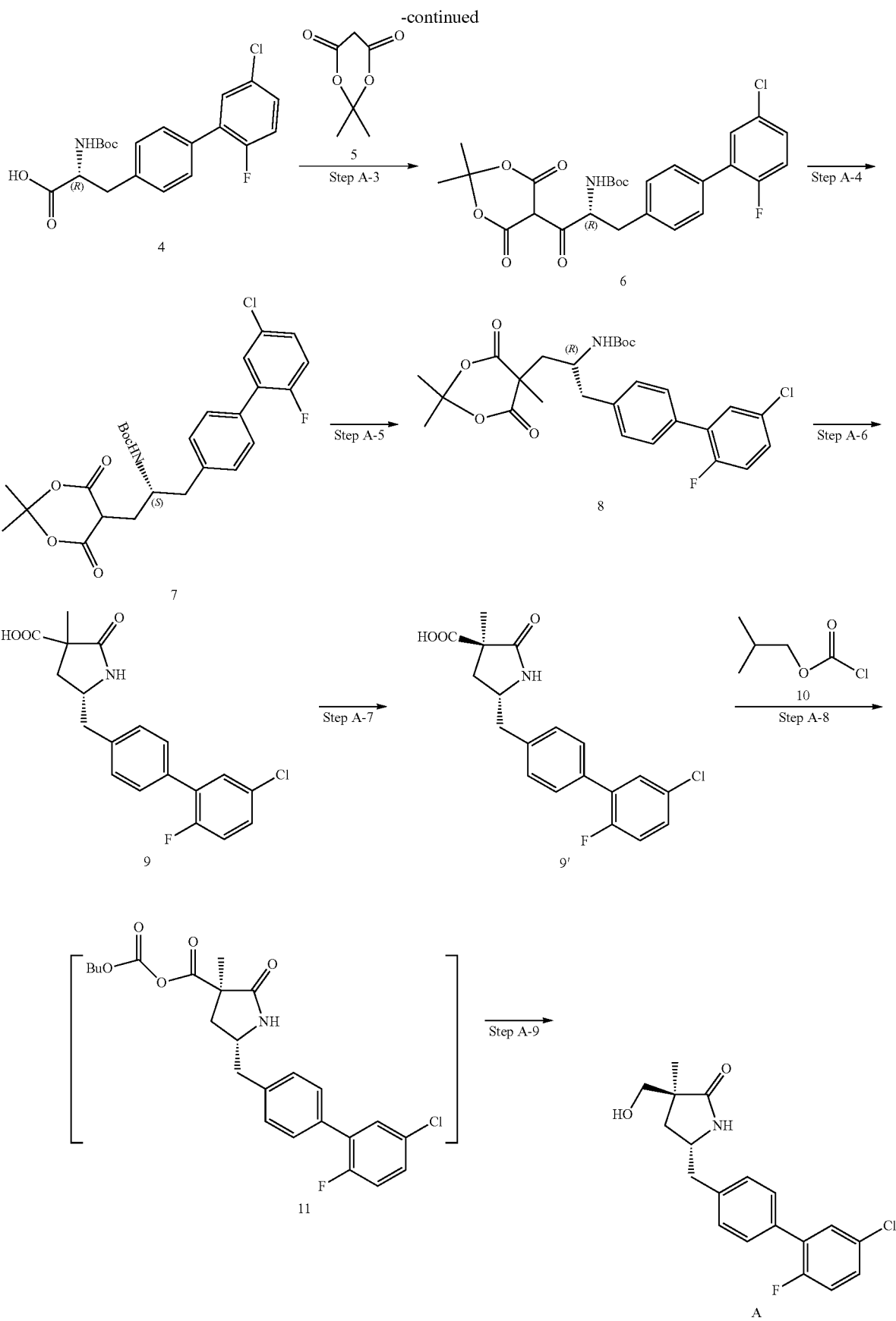

General reaction steps in Scheme A are as follows. The amine group of compound 1 is first protected by dissolving 1 in solvent with an aqueous base under an inert atmosphere at low temperature followed by the addition of an amine protecting agent in solvent at room temperature prior to isolation. A molar equivalence of approximately 1:2:1 of 1 to base to amine protecting agent may be used. Solvents that may be used for the reaction of 1 with the amine protecting agent include, but are not limited to, polar aprotic solvents, such as acetonitrile. Bases include, but are not limited to, strong bases including LiOH, NaOH, and KOH. Low temperatures are typically at or below −10° C.

Compound 2 is next coupled with 3 in solvent with the addition of an amphoteric compound, e.g., $NaHCO_3$ in water, and a catalyst such as $Pd(PPh_3)_4$ under an inert atmosphere. This results in derivative 4 which is then reacted with 5 in an aprotic solvent with a nucleophilic catalyst under an inert atmosphere. A peptide coupling agent is further used to form compound 6. Compound 6 is then placed in solvent with a weak acid under inert atmosphere and a reducing agent is added at low temperature (at or below −5° C.). This mixture is allowed to stir for several hours before being quenched with brine. Compound 7 is then isolated by extraction with a solution of a weak base and dried with drying agent prior to concentration under vacuum.

Compound 7 is next methylated in an aprotic solvent with weak base using a methylating agent such as MeI. The solid formed is isolated and further dissolved in solvent prior to being dried with a drying agent and concentrated under vacuum to yield compound 8. Compound 8 is further reacted with acid in an ether solvent to yield compound 9, which is then concentrated and washed with additional solvent to yield compound 9'. Compound 9' is then placed under an inert atmosphere in a polar aprotic solvent and reacted with 10 at low temperatures (<−5° C.) to give intermediate 11. Compound A is formed by reacting 11 with an organic base followed by reacting with 10 at low temperature and reduction with a reducing agent.

(2S,4R)-benzyl 4-amino-5-(5'-chloro-2'-fluoro-[1,1'-biphenyl]-4-yl)-2-(ethoxymethyl)-2-methylpentanoate (B) employed in this invention can be prepared from previously made starting material (A) and reagents using the procedures described in Example 2 and as shown in Scheme B:

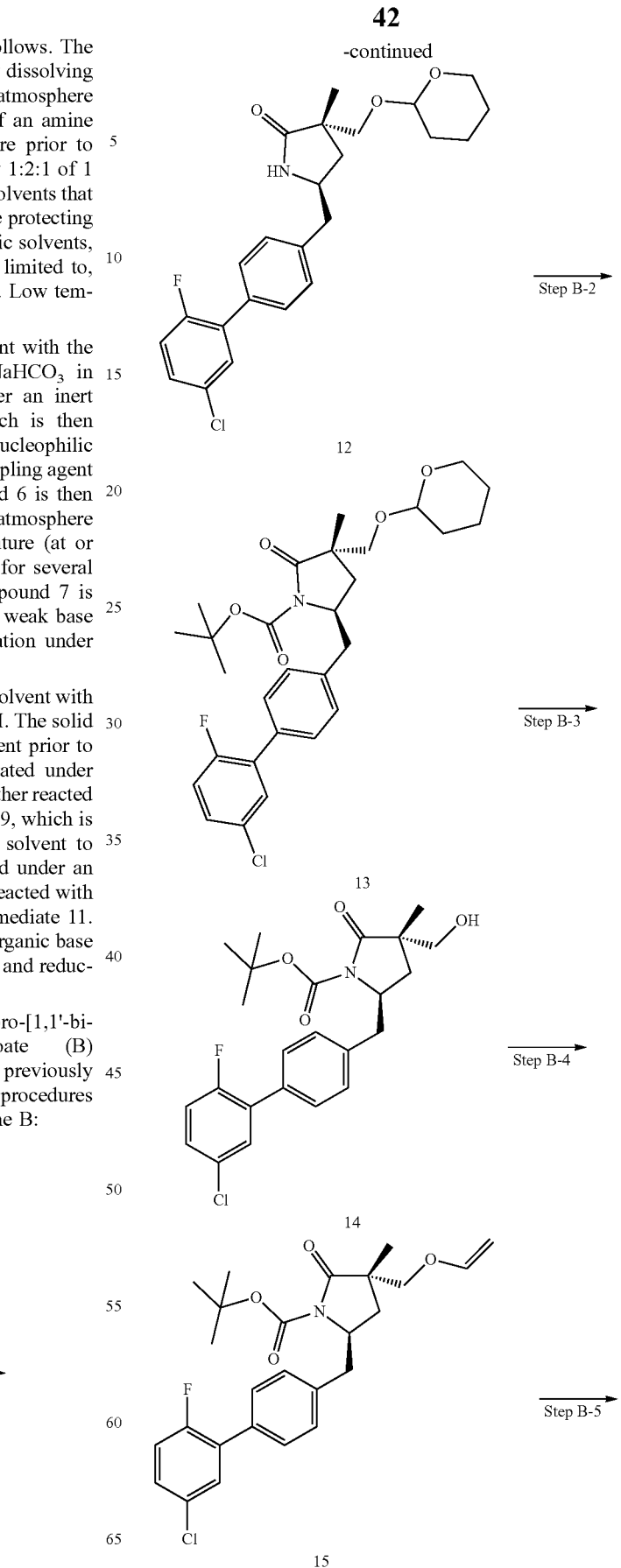

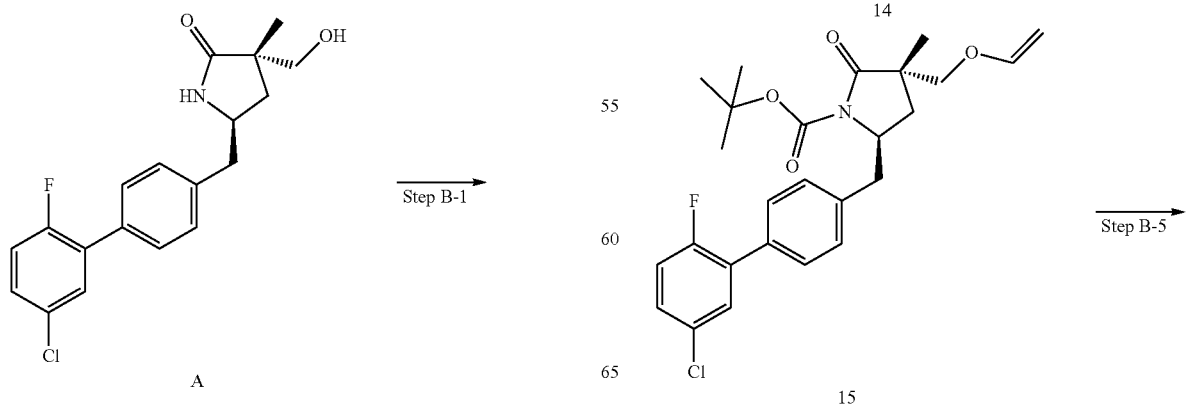

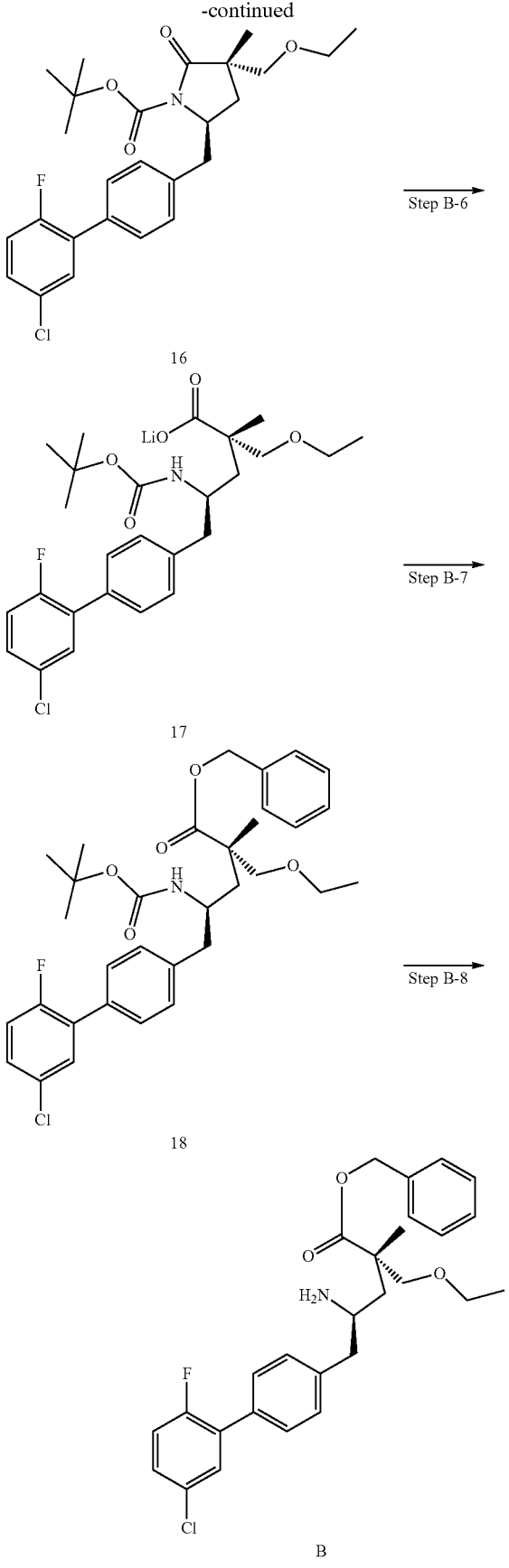

General reaction steps in Scheme B are as follows. Compound A is first reacted with 3,4-dihydro-2H-pyran in a solvent containing an acid prior to neutralization and isolation. The resultant crude mixture is placed in an ether solvent and stirred at low temperature to form a slurry. The slurry is further rinsed, dried and concentrated to viscous oil 12 prior to protecting the ring nitrogen with di-tert-butyl dicarbonate to form 13 under standard conditions. The ether group in 13 is further cleaved with a strong acid to form an alcohol group as shown in 14. Compound 14 is then reacted with ethyl vinyl ether by the addition of a heterocyclic organic ligand, e.g., 1,10-phenanthroline, in an inert atmosphere, followed by the addition of metal catalyst, e.g., palladium catalyst. The alkene group in purified product 15 is reduced using, e.g., H2 and 10% Pd/C, to yield 16. Ring opening of the pyrrolidone (saponification) in 16 is accomplished with an aqueous base prior to purification and isolation to yield compound 17. The carboxylate group in 17 is further protected, e.g., with benzyl bromide, under standard conditions to form 18. This is done prior to deprotecting the amine group of 18 to form compound B.

As discussed above, exemplary reaction conditions for Schemes A and B are described below in Examples 1 and 2, respectively.

Example 1

Synthesis of (3S,5R)-5-[[4-(5-Chloro-2-fluorophenyl)phenyl]methyl]-3-(hydroxymethyl)-3-methylpyrolidin-2-one (A)

Step A-1:

A solution of (2R)-2-amino-3-(4-bromophenyl)propanoic acid (1) (3300 g, 13.52 mol) in acetonitrile (46.2 L) was placed in a 250 L reactor that was purged and maintained with an inert atmosphere of nitrogen. A solution of NaOH (1081 g, 27.02 mol) in water (46.2 L) was added in several batches at −10° C. This was followed by the addition of a solution of di-tert-butyl dicarbonate (2948 g, 13.51 mol) in ACN (6.6 L). The resulting solution was stirred overnight at room temperature and further concentrated under vacuum. This resulting solution was diluted with 45 L of water/ice and the pH value of the solution was adjusted to pH 2 with 1N HCl. The resulting solution was then extracted with 3×50 L of DCM and the organic layers combined. The resulting mixture was washed with 1×50 L of brine and dried over anhydrous MgSO₄ and concentrated under vacuum. This resulted in 3720 g (80%) of (2R)-3-(4-bromophenyl)-2-[[(tert-butoxy)carbonyl]amino]propanoic acid (2) as a white solid.

Step A-2:

A solution of (2R)-3-(4-bromophenyl)-2-[[(tert-butoxy)carbonyl]amino]propanoic acid (2) (530 g, 1.54 mol) in dioxane (9.54 L), (5-chloro-2-fluorophenyl) boronic acid (3) (348 g, 2.00 mol), a solution of Na₂CO₃ (228 g, 2.15 mol) in water (1.06 L), and Pd(PPh₃)₄ (8.89 g, 7.69 mmol) was placed into a 20 L 4-necked round-bottom flask that was purged and maintained with an inert atmosphere of nitrogen. The resulting solution was heated to reflux for 2.5 h in an oil bath and then cooled to room temperature with a water/ice bath. The resulting solution was diluted with 15 L of EtOAc and washed with 1×5 L of 1N HCl and 4×5 L of brine. The combined organic extracts were dried over anhydrous MgSO₄ and concentrated under vacuum. The residue was washed with 2×1 L of PE. This resulted in 510 g (84%) of (2R)-2-[[(tert-butoxy)carbonyl]amino]-3-[4-(5-chloro-2-fluorophenyl)phenyl]propanoic acid (4) as brown oil.

Step A-3:

A solution of (2R)-2-[[(tert-butoxy)carbonyl]amino]-3-[4-(5-chloro-2-fluorophenyl)phenyl]propanoic acid (4) (510 g, 1.29 mol) in DCM (5000 mL), 2,2-dimethyl-1,3-dioxane-4,6-dione (5) (205 g, 1.42 mol), and 4-dimethylaminopyridine (237 g, 1.94 mol) was placed into a 10 L 4-necked round-bottom flask purged and maintained with an inert atmosphere of nitrogen. This was followed by the addition of a solution of DCC (294 g, 1.43 mol) in DCM (600 mL) dropwise with stirring at −10° C. The resulting solution was stirred overnight at room temperature and solids removed by filtration. The filtrate was washed with 1 N HCl (2 L) and brine (3 L). The combined organic extracts were dried over anhydrous MgSO$_4$ and solids were removed by filtration. The filtrate, tert-butyl N-[(2R)-3-[4-(5-chloro-2-fluorophenyl)phenyl]-1-(2,2-dimethyl-4,6-dioxo-1,3-dioxan-5-yl)-1-oxopropan-2-yl]carbamate (6), was used directly in the next step without further purification.

Step A-4:

A solution of tert-butyl N-[(2R)-3-[4-(5-chloro-2-fluorophenyl)phenyl]-1-(2,2-dimethyl-4,6-dioxo-1,3-dioxan-5-yl)-1-oxopropan-2-yl]carbamate (6) in DCM (7 L) and AcOH (600 mL) was placed into a 20 L 4-necked round-bottom flask purged and maintained with an inert atmosphere of nitrogen. This was followed by the addition of NaBH$_4$ (88.8 g, 2.35 mol) in several batches at −5° C. The resulting solution was stirred for 3 h at −5° C. in an ice/salt bath and then quenched by the addition of 1 L of brine in a dropwise manner. The resulting solution was diluted with 2 L of brine and washed with 2×2 L of water and 1×1 L of Na$_2$CO$_3$ and 1×2 L of brine. The combined organic extracts were dried over anhydrous MgSO$_4$ and concentrated under vacuum. This resulted in 520 g (79%) of tert-butyl N-[(2S)-1-[4-(5-chloro-2-fluorophenyl)phenyl]-3-(2,2-dimethyl-4,6-dioxo-1,3-dioxan-5-yl)propan-2-yl]carbamate (7) as a yellow oil.

Step A-5:

A solution of tert-butyl N-[(2S)-1-[4-(5-chloro-2-fluorophenyl)phenyl]-3-(2,2-dimethyl-4,6-dioxo-1,3-dioxan-5-yl)propan-2-yl]carbamate (7) (520 g, 1.03 mol) in acetone/DMF (1:1) (5.2 L), Na$_2$CO$_3$ (163 g, 1.54 mol), and MeI (219 g, 1.54 mol) was placed into a 10 L 4-necked round-bottom flask purged and maintained with an inert atmosphere of nitrogen. The resulting solution was stirred overnight at room temperature and then diluted with 15 L of water. After stirring for 1 h the solids were collected by filtration. The residue was dissolved in 5 L of DCM. The combined organic extracts were dried over anhydrous MgSO$_4$ and concentrated under vacuum. This resulted in 520 g (97%) of tert-butyl N-[(2R)-1-[4-(5-chloro-2-fluorophenyl)phenyl]-3-(2,2,5-trimethyl-4,6-dioxo-1,3-dioxan-5-yl)propan-2-yl]carbamate (8) as a yellow solid.

Steps A-6 and A-7:

A solution of tert-butyl N-[(2R)-1-[4-(5-chloro-2-fluorophenyl)phenyl]-3-(2,2,5-trimethyl-4,6-dioxo-1,3-dioxan-5-yl)propan-2-yl]carbamate (8) (520 g, 1.00 mol, 1.00 equiv) in CPME (2.6 L) was placed into a 10 L 4-necked round-bottom flask purged and maintained with an inert atmosphere of nitrogen. This was followed by the addition of HCl/CPME (4N) (2.6 L) at −5° C. The resulting solution was stirred overnight at room temperature. The resulting mixture was concentrated to half of the volume under vacuum. The solids were collected by filtration, and further washed with EtOAc/DIPE (1:2). This resulted in 220 g (61%) of (3R,5R)-5-[[4-(5-chloro-2-fluorophenyl)phenyl]methyl]-3-methyl-2-oxopyrrolidine-3-carboxylic acid (9') as a off-white solid.

Steps A-8 and A-9:

A solution of (3R,5R)-5-[[4-(5-chloro-2-fluorophenyl)phenyl]methyl]-3-methyl-2-oxopyrrolidine-3-carboxylic acid (9') (218 g, 602.55 mmol) in THF (4 L), NMM (170 g, 1.68 mol) was placed into a 10 L 4-necked round-bottom flask purged and maintained with an inert atmosphere of nitrogen. This was followed by the addition of 2-methylpropyl chloroformate (164.4 g, 1.20 mol) dropwise with stirring at −5° C. The resulting solution was stirred for an additional 20 min at −5° C. in an ice/salt bath. A solution of NaBH$_4$ (91.5 g, 2.42 mol) in water (400 mL) was further added dropwise with stirring at −5° C. and stirred for an additional 1 h at room temperature. The reaction was then quenched by the dropwise addition of 2.6 L of 1N HCl. The resulting mixture was stirred further for 1 h and then concentrated under vacuum to remove THF. The residual mixture was then stirred for another 1 h, and then the solids were collected by filtration. The solid was washed with water, dissolved in THF, dried over anhydrous Na$_2$SO$_4$ and concentrated under vacuum. This resulted in 170 g (81%) of (3S,5R)-5-[[4-(5-chloro-2-fluorophenyl)phenyl]methyl]-3-(hydroxymethyl)-3-methylpyrrolidin-2-one (A) as a white solid.

Example 2

Synthesis of (2S,4R)-Benzyl 4-amino-5-(5'-chloro-2'-fluoro-[1,1'-biphenyl]-4-yl)-2-(ethoxymethyl)-2-methylpentanoate (B)

Step B-1:

In a 5000 mL jacketed round-bottomed flask, (3S,5R)-5-((5'-chloro-2'-fluoro-[1,1'-biphenyl]-4-yl)methyl)-3-(hydroxymethyl)-3-methylpyrrolidin-2-one (A) (121.0 g, 348 mmol) and DCM (2420 mL) were added to give a homogenous clear solution which was then cooled to 0° C. with stirring. 3,4-dihydro-2H-pyran (71.0 mL, 783 mmol) and 4-methylbenzenesulfonic acid (20.97 g, 122 mmol) were added and reaction mixture was stirred at 18.5° C. overnight to achieve >98% conversion. The reaction mixture was then quenched with 2420 mL of saturated NaHCO$_3$, phases were slowly separated, the organic layer was dried over sodium sulfate, filtered and solvent removed. The crude mixture was then placed in DIPE (1815 mL) with stirring at 21° C. over 1 h then cooled & stirred at 0-5° C. over 5 h to yield a white slurry. The slurry was filtered and rinsed with 1× volume of cold (0° C.) DIPE and filtered. The resultant solids were dried overnight to yield 113.8 g; 99.1% HPLC purity. The filtrate was further dried to yield a thick oil weighing 24 g. DIPE (96 mL) was added and the mixture was stirred overnight at 0-5° C. to yield (3S,5R)-5-((5'-Chloro-2'-fluoro-[1,1'-biphenyl]-4-yl)methyl)-3-methyl-3-(((tetrahydro-2H-pyran-2-yl)oxy)methyl)pyrrolidin-2-one (12).

Step B-2:

In a 5000 mL jacketed round-bottomed flask, (3S,5R)-5-((5'-chloro-2'-fluoro-[1,1'-biphenyl]-4-yl)methyl)-3-methyl-3-(((tetrahydro-2H-pyran-2-yl)oxy)methyl)pyrrolidin-2-one (12) (113.8 g, 263 mmol) and THF (1707 mL) were added with stirring to give a clear homogeneous solution that was purged with nitrogen and cooled to −10° C. 1M NaHMDS in THF (290 mL, 290 mmol) was added dropwise at temperature below 0° C. and reaction mixture was stirred for 30 minutes. Di-tert-butyl dicarbonate (69.0 g, 316 mmol) was dissolved by dropwise addition in 3 times its volume in THF (207 mL) at a temperature below 10° C. The reaction mixture was stirred at 20° C. overnight and quenched with 20% ammonium chloride solution (2731 mL). EtOAc (1821 mL) was added and the phases were separated into an aqueous layer (pH 9) and an organic layer. The organic layer was washed with brine (2731 mL) and the phases separated again into an aqueous phase (pH 7) and an organic layer, where the organic layer was dried with $Na_2SO_4$ prior to filtration. The solvent was removed yielding a thick oil. Upon further drying overnight, foam-containing solid of (3S,5R)-tert-butyl 5-((5'-chloro-2'-fluoro-[1,1'-biphenyl]-4-yl)methyl)-3-methyl-2-oxo-3-(((tetrahydro-2H-pyran-2-yl)oxy)methyl)pyrrolidine-1-carboxylate (13) was produced (146.5 g, 275 mmol, 105% yield, 98.76% purity).

Step B-3:

(3S,5R)-tert-butyl 5-((5'-chloro-2'-fluoro-[1,1'-biphenyl]-4-yl)methyl)-3-methyl-2-oxo-3-(((tetrahydro-2H-pyran-2-yl)oxy)methyl)pyrrolidine-1-carboxylate (13) (146.5 g, 275 mmol) and MeOH (1465 mL) were added to a 3000 mL round-bottomed flask. 4-methylbenzenesulfonic acid, $H_2O$ (3.93 g, 20.65 mmol) was further added and reaction mixture was stirred at 0° C. for 16 h to achieve >97% conversion. To the completed reaction, EtOAc (2930 mL) was added and followed by distillation, with bath temperature below 30° C., to achieve a reduction of the total volume to approximately 293 mL. To the concentrated solution, EtOAc (2930 mL) was added again and distilled down to approximately 293 mL. A final wash was completed by adding EtOAc (2930 mL) and distilled to a final volume of 1465 mL to completely remove any residual methanol. The remaining acid was quenched by washing the final volume above (1465 mL) with EtOAc containing 10% $NaHCO_3$ (1465 mL) with stirring over 30 min at a temperature ≤21° C. The layers were allowed to separate by turning off the stirring (aqueous layer pH-7). The organic layer was washed with 1465 mL of brine and allowed to separate (aqueous layer pH=7). The ethyl acetate layer was then vacuum dried to ~146.5 mL before 1465 mL hexanes were slowly added to cloud point. The solution was allowed to sit for 1 h followed by addition of 1465 mL hexanes. The mixture was stirred overnight at 0° C. and the solids were filtered and washed with 293 mL hexanes. The remaining solids were dried overnight under high vacuum to yield 98.4 g of (3S,5R)-tert-Butyl 5-((5'-chloro-2'-fluoro-[1,1'-biphenyl]-4-yl)methyl)-3-(hydroxymethyl)-3-methyl-2-oxopyrrolidine-1-carboxylate (14); 80% Yield; 99.3% HPLC purity.

Step B-4:

(3S,5R)-tert-butyl 5-((5'-chloro-2'-fluoro-[1,1'-biphenyl]-4-yl)methyl)-3-(hydroxymethyl)-3-methyl-2-oxopyrrolidine-1-carboxylate (14) (118.2 g, 264 mmol) and DCM (591 mL) were added to a 100 mL round-bottomed flask to form a colorless solution. Ethyl vinyl ether (761 mL, 7916 mmol) and 1,10-phenanthroline (4.76 g, 26.4 mmol) were added to the vessel and purged with N2, followed by the addition of Pd(II)acetate (8.89 g, 39.6 mmol). The reaction mixture was stirred at room temperature for 20 h to achieve ~81% conversion. The solvent was removed by rotoevaporation to afford a crude product that was purified by column chromatography. The column was pre-conditioned with 100% hexanes and the crude product (30 g/run) was dissolved in DCM and loaded onto 300 g of a silica gel packed column. An isocratic gradient with 40% ethyl acetate/hexanes was used to elute the compound, yielding 91.25 g of purified (3S,5R)-tert-Butyl 5-((5'-chloro-2'-fluoro-[1,1'-biphenyl]-4-yl)methyl)-3-methyl-2-oxo-3-((vinyloxy)methyl)pyrrolidine-1-carboxylate (15).

Step B-5:

(3S,5R)-tert-butyl 5-((5'-chloro-2'-fluoro-[1,1'-biphenyl]-4-yl)methyl)-3-methyl-2-oxo-3-((vinyloxy)methyl)pyrrolidine-1-carboxylate (15) (185 g, 390 mmol) was dissolved in THF (1900 mL) and acetic acid (11.17 mL) was added followed by N2 purge over 10 min. The mixture was then bubbled with $H_2$ and 10% Pd/C (or 18.5 g) was added. A slow $H_2$ (gas) purge was continued overnight at 22° C. until the reaction reached completion as measured by HPLC. The reaction mixture was filtered through celite to yield a homogeneous solution. The filtrate was then pumped to dryness under high vacuum to afford 185 grams of (3S,5R)-tert-Butyl 5-((5'-chloro-2'-fluoro-[1,1'-biphenyl]-4-yl)methyl)-3-(ethoxymethyl)-3-methyl-2-oxopyrrolidine-1-carboxylate (16); 89% HPLC; 99% yield.

Step B-6:

(3S,5R)-tert-butyl 5-((5'-chloro-2'-fluoro-[1,1'-biphenyl]-4-yl)methyl)-3-(ethoxymethyl)-3-methyl-2-oxopyrrolidine-1-carboxylate (16) (185 g, 389 mmol) and ~1205 mL THF were added in a 3000 mL round-bottomed flask to give a colorless solution. Approximately 1205 mL of 1M LiOH in $H_2O$ was added and reaction mixture was stirred at RT overnight to complete saponification. Approximately 1205 mL EtOAc was added to the overnight reaction mixture (pH=13) and then washed with approximately 1205 mL of saturated aqueous $NH_4Cl$. Phases were separated into an aqueous phase (pH=8) and an organic phase with the product remaining in the organic layer. The organic layer was then washed with brine, layers again separated and the organic layer dried over $Na_2SO_4$ before being filtered and vacuum dried to yield lithium (2S,4R)-4-((tert-butoxycarbonyl)amino)-5-(5'-chloro-2'-fluoro-[1,1'-biphenyl]-4-yl)-2-(ethoxymethyl)-2-methylpentanoate (17) (213 g, 426 mmol, 94.6% yield).

Step B-7:

Lithium (2S,4R)-4-((tert-butoxycarbonyl)amino)-5-(5'-chloro-2'-fluoro-[1,1'-biphenyl]-4-yl)-2-(ethoxymethyl)-2-methylpentanoate (17) (194.0 g, 393 mmol) and ~650 mL DMF were into a 2 L round-bottomed flask to give a colorless solution. $K_2CO_3$ (81 g, 589 mmol) was added and reaction mixture was stirred for 15 min at room temperature. Benzyl bromide (56.1 mL, 471 mmol) was then added in one portion and reaction mixture was stirred at approximately 22° C. overnight. Complete conversion was accomplished after 20 h as measured by LCMS or TLC. Approximately 3900 mL of $NH_4Cl$ and approximately 650 mL of EtOAc were added and stirred over 15 min, and phases were separated. The organic layer was washed with ~3900 mL of brine, layers separated again, and the organic layer dried with sodium sulfate followed by solvent removal. Crude product was purified on $SiO_2$ 0-25% EtOAc/hexanes and the combined purified fractions yielded (2S,4R)-benzyl 4-((tert-butoxycarbonyl)amino)-5-(5'-chloro-2'-fluoro-[1,1'-biphenyl]-4-yl)-2-(ethoxymethyl)-2-methylpentanoate (18) (190 g, 322 mmol, 82% yield). MS m/z {M+H}$^+$ calc'd for $C_{33}H_{39}ClFNO_5$, 584.118; found 584.12.

Step B-8:

(2S,4R)-benzyl 4-((tert-butoxycarbonyl)amino)-5-(5'-chloro-2'-fluoro-[1,1'-biphenyl]-4-yl)-2-(ethoxymethyl)-2-methylpentanoate (18) was charged into a 3 L round-bottomed flask was added (190.0 g, 325 mmol). 3M HCl in CPME (1084 mL, 3253 mmol) was added and reaction mixture was stirred at room temperature over 50 h to yield a slurry at >99% conversion. Approximately 1084 mL of fresh CPME was added and resulting slurry was stirred over 3 h prior to filtering. The solids were rinsed with ~250 mL of cold (0° C.) CPME. The solids were then dried under N2 gas to yield a white solid as (2S,4R)-benzyl 4-amino-5-(5'-chloro-2'-fluoro-[1,1'-biphenyl]-4-yl)-2-(ethoxymethyl)-2-methylpentanoate (B), HCl (150 g, 288 mmol, 89% yield, 99.5% purity). MS m/z {M+H}⁺ calc'd for $C_{28}H_{31}ClFNO_3$, 484.00; found 520.46 (HCl salt).

Example 3

(2S,4R)-5-(5'-Chloro-2'-fluoro-[1,1'-biphenyl]-4-yl)-2-(ethoxymethyl)-4-(3-hydroxyisoxazole-5-carboxamido)-2-methylpentanoic Acid (Compound I)

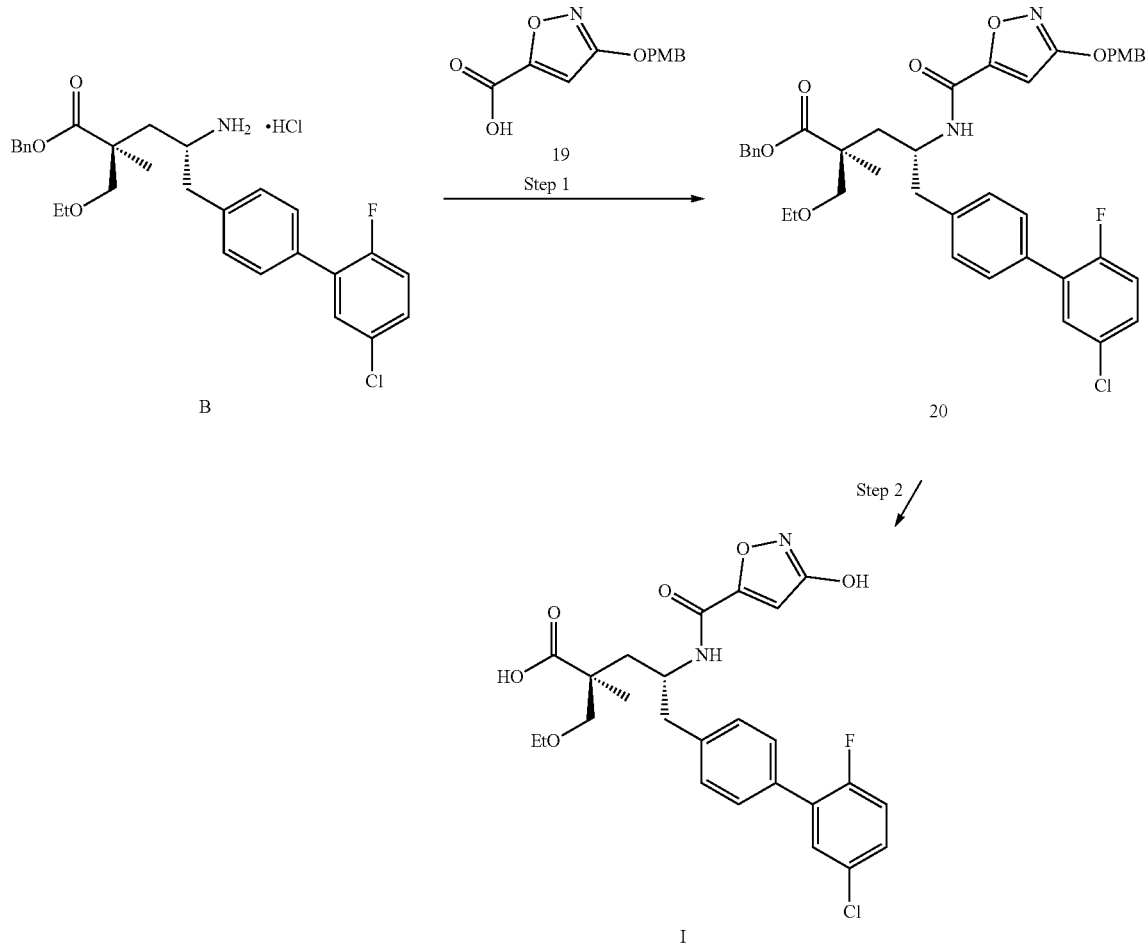

Step 1:

Benzyl (2S,4R)-4-amino-5-(5'-chloro-2'-fluoro-[1,1'-biphenyl]-4-yl)-2-(ethoxymethyl)-2-methylpentanoate hydrochloride (B) (2.95 kg, 5668 mmol) was coupled with 3-((4-methoxybenzyl)oxy)isoxazole-5-carboxylic acid (19) (1.48 kg, 5939 mmol) using HCTU (2.71 kg, 6551 mmol) and DIPEA (0.28 kg, 2180 mmol) in THF (26.64 kg). The mixture was cooled to <10° C. DIPEA (2.24 kg, 17.332 mmol) was then added to the mixture at a temperature below 10° C. and the mixture was adjusted to a temperature of 20° C.±10° C. and stirred for at least 1 h until completion. EtOAc (26.55 kg) was added next to the mixture, followed by the addition of USP water (29.5 kg) at a temperature below 30° C. The mixture was then agitated for at least 30 min at a temperature of 20° C.±10° C. and allowed to settle for at least 30 min. The lower aqueous layer was split into containers. A 5 w/w % NaHCO₃ solution (30.4 kg) was added to the mixture at a temperature below 30° C., further agitated for at least 30 min at a temperature of 20° C.±10° C., and settled for at least 30 min. The lower aqueous layer was split into containers. The NaHCO₃ step was repeated two more times and the mixture was then sampled for 6-chloro-1-hydroxybenzotriazole content. A 10 w/v % NaCl (31.6 kg) solution was added to the mixture at a temperature below 30° C., agitated for at least 30 min at a temperature of 20° C.±10° C., and then settled for at least 30 min. The lower aqueous layer was split into containers. The remaining layer was distilled to about 9 L while maintaining batch temperature below 30° C. EtOAc (39.8 kg) was then added to the mixture and vacuum distillation was used to reduce the volume of the mixture to about 9 L while maintaining the batch temperature below 30° C. EtOAc (10.3 kg) was again added to the mixture and the mixture stirred for at least 10 min. The mixture in the first reaction vessel was then transferred through an inline filter to a second reaction vessel. EtOAc (5.6 kg) was used to rinse the first reaction vessel and transferred through an inline filter to the second reaction vessel. The product, benzyl (2S,4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate (20) (4.05 kg; 5663 mmol), in reaction vessel two was mixed for at least 10 min and drained into sterile Nalgene containers and stored between 0-10° C. until further processing.

Step 2:

Pd/C, 10% w/w (0.42 kg), was charged to reaction vessel one along with benzyl (2S,4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate (20) (4.05 kg; 5663 mmol). Denatured ethanol (27.5 kg) was then added to reaction vessel one and the components were mixed at 20-30° C. for at least 5 min. A scrubber containing NaOH was used to process the HCl gas evolved during this step. 6M HCl (3.1 kg) was added to the reaction while maintaining temperature of <30° C. and mixed for at least 5 min. The mixture was degassed by applying vacuum and concurrently supplying nitrogen. The temperature of the mixture was then adjusted to 20-30° C. and the reaction vessel was evacuated. $H_2$ (5.0 ultra-high purity) was bubbled through the mixture until reaction was completed. Hydrogen supply was shut off, the mixture purged with nitrogen and transferred through an inline filter to a second reaction vessel. Denatured ethanol (6.5 kg) was charged to the first reaction vessel as a rinse and transferred through the inline filter to the second reaction vessel. The mixture in the second reaction vessel was then distilled using vacuum to about 41 L while maintaining the temperature below 30° C. The temperature was adjusted to 20-30° C. and a 30% w/w $H_2O_2$ solution (0.36 kg) was added to the mixture in the second reaction vessel while maintaining the temperature <25° C. The mixture was stirred for at least 16 h at 20-30° C. until reaction completion. The mixture in the second reaction vessel was distilled using vacuum to about 12 L while maintaining a temperature below 30° C. ACN (40.1 kg) was then added to this mixture and the mixture distilled using vacuum to about 12 L while maintaining the temperature below 30° C. (this step repeated). Next, ACN (3.2 kg) was again added to the mixture in the second reaction vessel and heated to 40-50° C. for at least 1 h. The mixture was cooled to 15-25° C. over at least 1.5 h and maintained at that temperature for at least 2 additional h before being filtered by centrifuge. ACN (13.0 kg) was then added to the first reaction vessel and used to wash the centrifuged solids. The centrifuged solids were then dried under vacuum at 20-30° C. for at least 16 h to yield (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (4,218 mmol; 2.13 kg; 74.5% Yield; 97.5% Purity).

Example 4

Preparation of Crystalline (2S,4R)-5-(5'-Chloro-2'-fluoro-[1,1'-biphenyl]-4-yl)-2-(ethoxymethyl)-4-(3-hydroxyisoxazole-5-carboxamido)-2-methylpentanoic Acid (Compound I')

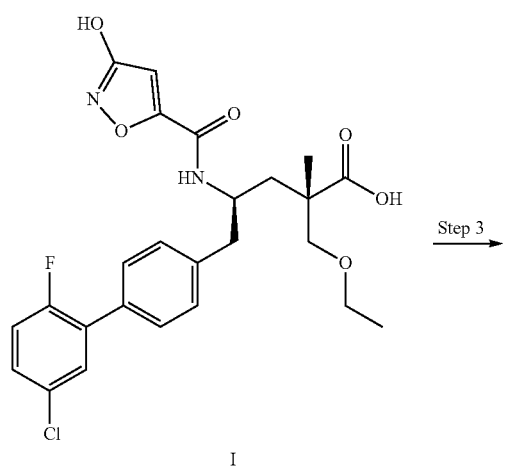

I

Step 3

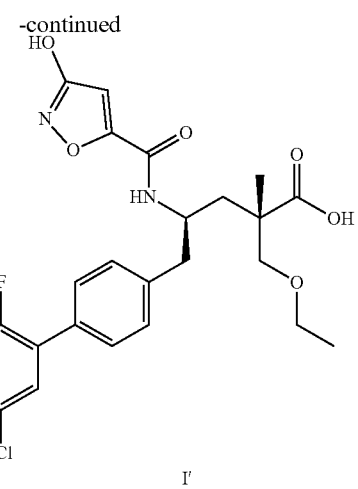

I'

Step 3:

Compound I (2.0 kg; 3961 mmol), EtOAc (36.0 kg) and USP water (20 kg) were added to a reaction vessel A and the resulting mixture was stirred for at least 30 min at 20±10° C. The batch was then settled for at least an additional 30 min. The lower aqueous layer was separated and stored in containers while the remaining non-aqueous phase was transferred through an inline filter to a reaction vessel B. EtOAc (3.6 kg) was added to reaction vessel A to rinse and transferred through an inline filter to the mixture in reaction vessel B. The mixture in reaction vessel B was then vacuum distilled to a reduced volume (6 L). An additional amount of EtOAc (25.2 kg) was added to reaction vessel A and transferred through an inline filter to the mixture in reaction vessel B. The mixture in reaction vessel B was then heated to a temperature of 75±5° C. and agitated for at least 5 min until solids dissolved. This mixture was then cooled to −10±5° C. over at least 6 h and additionally agitated for at least 12 h at −10±5° C. prior to filtration onto filter C. An additional amount of EtOAc (5.4 kg) was charged to reaction vessel A, further transferred through an inline filter to reaction vessel B, and cooled to −10±10° C. This solvent was then used to wash the filtrate on filter C. Filtrate and wash were then collected in containers. The filtrate or wet cake was dried under vacuum at 40° C.±10° C. for at least 16 h and then sampled for purity. Compound I' was ≥98.0% pure as measured by HPLC and EtOAc was present at ≤2.5% w/w as measured by gas chromatography. The yield of Compound I' after crystallization was (1.05 kg; 2079 mmol; 52.5% Yield; 98.5% Purity).

Example 5

Alternate Preparation of Crystalline (2S,4R)-5-(5'-Chloro-2'-fluoro-[1,1'-biphenyl]-4-yl)-2-(ethoxymethyl)-4-(3-hydroxyisoxazole-5-carboxamido)-2-methylpentanoic Acid (Compound I')

Compound I (4.9 kg; 9705 mmol), SiliaMetS® Thiol (1.62 kg) and EtOH (200 proof, 54.9 kg) were added to a reaction vessel A and the resulting mixture was stirred for at least 1 h at a temperature between about 25° C. to 35° C. The mixture was then filtered through celite and washed with EtOH (200 proof, 7.8 kg) and transferred to reaction vessel B using an in-line 0.22 μm filter and rinsed with EtOH (200 proof, 7.8 kg). The mixture in vessel B was further vacuum distilled to about 10% of its original volume at a temperature between about 40° C. to 60° C. The vessel containing the remaining mixture was adjusted to >50° C. prior to the addition of filtered (0.22 μm) USP purified water (49 kg). The mixture was next heated to a temperature of between about 75° C. to 85° C. with stirring until complete dissolution of the product. The mixture was cooled to a temperature of between about −5° C. to 5° C. over at least 4 h and stirred for at least an additional 16 h at the same temperature. The resultant mixture was then filtered and washed with a pre-cooled mixture of EtOH (200 proof, 9.8 kg) and USP water (12.3 kg). The temperature of the pre-cooled solvent mixture was adjusted to between about 0° C. to 10° C. The remaining filtrate was dried under vacuum at a temperature of between about 40° C. to 60° C. for at least 16 h and then sampled for solvent and purity by HPLC. The yield of Compound I' after crystallization was 90% (4.6 kg; 9110 mmol; ≥97.0% Purity).

Example 6

Stability Study of Crystalline (2S,4R)-5-(5'-Chloro-2'-fluoro-[1,1'-biphenyl]-4-yl)-2-(ethoxymethyl)-4-(3-hydroxyisoxazole-5-carboxamido)-2-methylpentanoic Acid (I')

One challenge in pharmaceutical drug development relates to discovering a stable, crystalline form of a drug having a reasonably high melting point. One challenge of the present invention was that small crystals of the free acid of Compound I were difficult to obtain with the favorable physical properties mentioned above. Once achieved, the small crystals melted around 216° C. and an accelerated stability study of Compound I' was conducted at the temperatures and % relative humidity (RH) reported below.

ASSAYS

Assay 1: IV/PO Pharmacokinetic Study in Rats, Dogs and Monkeys

Each rat, dog or monkey PK study began with formulation of the test compound. Appropriate masses of each test compound were added into a volume of vehicle (e.g. 5% sodium bicarbonate, 5% dextrose in $H_2O$) such that the final concentration of each compound was appropriate to be dosed. Although a homogenous suspension were acceptable for oral dosing, intravenous dosing solutions were sterile-filtered (0.2 μm) prior to dosing to ensure no particulates were administered.

In the rat study, pre-cannulated male Sprague-Dawley rats (3 per route) were obtained from Harlan Laboratories or Charles Rivers Laboratories. Rats received either a oral dose delivered into the stomach using a syringe and gavage tube or a intravenous (via lateral tail vein) dose of the dosing solution. The final dose was 0.5 mg/kg. Serial blood samples were harvested via the cannula implanted in the jugular vein at 3 min, 15 min, 30 min, 1 h, 2 h, 4 h, 6 h, and 24 h post-dose. Sampling was performed either manually or using automated blood samplers. Samples were collected into microtainer tubes containing EDTA as the anticoagulant and were processed to plasma by refrigerated centrifugation.

In the dog study, male non-naïve beagle dogs (3 per route) housed at Agilux Laboratories (Worcester, Mass.) and weighing between 9-14 kg received either an oral or intravenous dose. Oral doses were delivered into the stomach using a syringe and gavage tube followed by a water flush of approximately 10 mL. Oral doses were administered at a volume of 2 mL/kg. Intravenous doses were administered via a percutaneous catheter placed in sphenous vein followed by a saline flush of approximately 3 mL. Intravenous

|  | 25° C., 60% RH | | | 40° C., 75% RH[a] | | |
|---|---|---|---|---|---|---|
| Time (months) | Assay[b] | Total Impurities/ Degradants (% area) | Water Content (% w/w) | Assay[b] | Total Impurities/ Degradants (% area) | Water Content (% w/w) |
| 0 | 98.6 | 0.87 | <LOQ (LOQ = 0.2%) | 98.6 | 0.87 | <LOQ (LOQ = 0.2%) |
| 1 | nt[b] | nt | nt | 98.5 | 0.86 | nt |
| 3 | 98.5 | 0.86 | nt | 98.6 | 0.87 | <LOQ (LOQ = 0.22%) |
| 6 | 99.2 | 0.87 | <LOQ (LOQ = 0.19%) | 99.0 | 0.87 | <LOQ (LOQ = 0.19%) |
| 9 | 99.0 | 0.87 | nt | nt | nt | nt |
| 12 | 99.2 | 0.87 | <LOQ (LOQ = 0.19%) | nt | nt | nt |
| 18 | 99.1 | 0.87 | nt | nt | nt | nt |

RH = relative humidity; nt =not tested; LOQ = limit of quantification
[a] Accelerated storage conditions, measured for 6-months and generally accepted as equivalent to 2-years at 25° C., 60% relative humidity.
[b] Assay = (mass substance/total mass) * 100 = % (w/w).

These data demonstrate that Compound I' remains stable for at least 18-months at 25° C., 60% RH and for at least 2-years measured by accelerated conditions of 40° C., 75% RH. These data also show that no quantifiable amount of water is detected at 12-months, thus indicating that the crystals remain non-hygroscopic over that time period. Additionally, these data indicate that no more than 1% total impurities/degradants are detected over 18-months (25° C., 60% RH) or 2-years (accelerated conditions of 40° C., 75% RH).

doses were administered at a volume of 0.5 mL/kg. The final dose for either IV or PO was 0.1 mg/kg. Serial blood samples were harvested via direct venipuncture at 3 min, 15 min, 30 min, 1 h, 2 h, 4 h, 6 h, 8 h, 12 h, and 24 h post-dose. All samples were collected manually into microtainer tubes containing EDTA as the anticoagulant and were processed to plasma by refrigerated centrifugation.

A monkey PK study was performed with an appropriate mass of Compound I in volume of vehicle (e.g., 5% sodium bicarbonate, 5% dextrose in $H_2O$, pH 7.4, for oral and IV and filtered through a 0.22 μM PDVF syringe for IV) such that the final concentration was dosed at 1.0 mg/mL for both IV and PO.

Male cynomolgus monkeys (3 per route) housed at Xenometrics (Stilwell, Kans.) received an IV or PO dose of Compound I at 1 or 2 mg/kg. Intravenous doses of Compound I were administered through an indwelling catheter in the cephalic vein followed by a saline flush of approximately 3 mL. Intravenous doses were administered at a volume of 1 mL/kg. Oral doses were delivered into the stomach using a syringe and gavage tube followed by a water flush of approximately 10 mL. Oral doses were administered at a volume of 2 mL/kg. Blood samples were collected from each animal at each time point (pre-dose, 0.083 h, 0.25 h, 0.5 h, 1 h, 2 h, 4 h, 6 h, 8 h, 12 h, and 24 h) via the cephalic, femoral, or sphenous vein through 48 hours. All samples were collected into $K_2$EDTA tubes and placed on ice. Samples were processed to plasma by centrifugation (3200 rpm, 10 minutes, 5° C.), and acidified with a final concentration of 2% acetic acid. Aliquots of plasma were transferred to a 96-well plate tubes and stored frozen (−70° C.) prior to bioanalysis.

Plasma concentrations of Compound I were determined by LC/MS/MS. Plasma study samples were vortexed and placed in a 96-well plate. The samples were extracted with 200 μL of acetonitrile with an internal standard. The extract was centrifuged for 10 minutes at 2809 RPM and 50 μL supernatant was mixed with 200 μL 0.2% formic acid in water. Samples (10-15 μL) were injected on a ThermoFisher HyPURITY™ (C18 50×2.1 mm) column with a flow rate of 0.35 mL/min. Mobile phase A consisted of water:acetonitrile:formic acid (95:5:0.1, v:v:v) and Mobile phase B consisted of methanol:acetonitrile:formic acid (50:50:0.1, v:v:v) (dog). Mobile phase A consisted of 0.2% formic acid in water and mobile phase B consisted of 0.2% formic acid in acetonitrile (rat and monkey). Pharmacokinetic parameters of Compound I were determined by non-compartmental analysis (Model 201 and Model 200 for IV and PO administration, respectively) using Phoenix WinNonlin Version 6.3 (Certara, Sunnyvale, Calif.) and using individual plasma concentration time profiles from 3 animals per treatment group.

Plasma clearance was determined from the intravenous arm of the study, and represents the rate at which plasma is cleared of drug. It is equal to the dose divided by the area under the plasma concentration-time curve. In addition to plasma clearance, it is also essential for an orally administered drug to reach efficacious systemic levels following oral delivery. Oral bioavailability is a measurement of plasma exposures following oral administration relative to exposures following intravenous administration.

| | | Pharmacokinetic Data | | |
|---|---|---|---|---|
| Study | Route | $AUC_{last}$[a] (μg * hr/mL) Mean | $CL_{last}$[b] (L/hr/kg) Mean | Oral Bioavailability (%)[c] Mean |
| Rat | IV | 0.39 | 1.22 | — |
| (0.5 mg/kg) | PO | 0.13 | 3.01 | 33% ± 10.3% |
| Dog | IV | 0.21 | — | — |
| (0.1 mg/kg) | PO | 0.0349 | 2.83 | 16.5% ± 4.2% |
| Monkey | IV | 2.29 | 0.38 | — |

| | | Pharmacokinetic Data | | |
|---|---|---|---|---|
| Study | Route | $AUC_{last}$[a] (μg * hr/mL) Mean | $CL_{last}$[b] (L/hr/kg) Mean | Oral Bioavailability (%)[c] Mean |
| (IV: 1 mg/kg PO: 2 mg/kg) | PO | 1.91 | 1.31 | 41.8% ± 22.7% |

[a] $AUC_{last}$ is the area under the plasma concentration versus time curve from time 0 to the time after dosing at which the last quantifiable concentration was observed, estimated by linear trapezoidal method
[b] $CL_{last}$ is the dose divided by $AUC_{last}$
[c] Oral Bioavailability is calculated as $AUC_{last}$ following oral administration, divided by $AUC_{last}$ following intravenous administration, normalized for any differences in administered doses, expressed as a percentage This rat data shows that Compound I has an oral bioavailability of approximately 33% at a dose of 0.5 mg/kg. At higher doses (30-1000 mg/kg), mean bioavailability ranged from 49-79% in the rat (data not shown). Compound I was also administered with azilsartan in the rat species (data not shown). This dog data shows that Compound I has a limited oral bioavailability of approximately 17%. At higher doses (100-300 mg/kg), mean bioavailability ranged from 7-13% (data not shown). The monkey data shows that Compound I has an oral bioavailability of approximately 42%. At higher doses (30 and 100 mg/kg), mean bioavailability for three different formulations ranged from 55-83% (data not shown).

Assay 2: Renal Excretion of Compound I in Rat, Dog and Monkey Species

An important factor for insuring appropriate long term drug dosing and correct steady-state drug concentrations in patients is drug clearance. In general, decreased drug clearance results in higher drug concentrations and greater drug effects. In order to understand renal clearance of Compound I, the percent of administered dose recovered in urine following a single IV dose was assessed in three animal species. Three separate studies in male Sprague Dawley rats, male beagle dogs and male cynomolgus monkeys, respectively, were conducted and the procedure and experimental results are described below.

Male Sprague Dawley rats (N=6, two groups of 3), having body weights of 297 to 316 g and 294 to 311 g, received an IV dose of Compound I at 0.5 mg/kg (Group I) and 3.0 mg/kg (Group II) as part of a dosing cassette. Compound I was dissolved in 5% $NaHCO_3$ in D5W (5% dextrose in water, pH 7.8) at a concentration of 0.25 mg/mL yielding a final total concentration of 1.0 mg/mL to deliver a 0.5 mg/kg intravenous dose. Additionally, Compound I was dissolved in 5% $NaHCO_3$ in D5W (5% dextrose in water, pH 7.4) at a concentration of 1.5 mg/mL to deliver a 3 mg/kg intravenous dose. Both formulations were sterile filtered prior to intravenous administration. The rats had access to food according to their typical feeding schedules before and after administration of Compound I. For the cohort receiving 0.5 mg/kg of Compound I, urine was collected on dry ice. After the 24-hour urine collection period, urine samples were thawed, volume was recorded and samples were mixed prior to removal of an aliquot (~700 μL) for bioanalysis. For the cohort receiving 3.0 mg/kg of Compound I, urine was collected as above but glacial acetic acid was added to the collected urine aliquots to yield a final concentration of 2% acetic acid. All samples were stored frozen (−70° C.) prior to bioanalysis.

Rat urine concentrations of Compound I were determined by LC/MS/MS. Urine samples were thawed and diluted 5-fold in $K_2$EDTA rat plasma. A 50 μL aliquot of the diluted urine was transferred to a 96-well plate and extracted with 200 μL of acetonitrile containing an internal standard. The 96-well plate was centrifuged for 10 minutes at 2809 RPM and the supernatant was diluted five-fold with 0.2% formic acid in water transferred to a new 96-well plate. The supernatant was diluted in 0.2% formic acid in water. Samples (10 to 15 μL) were injected onto a Thermo Hypurity (C18 50×2.1 mm) column with a flow rate of 0.30 or 0.35 mL/min. Mobile phase A consisted of 0.2% formic acid in water and mobile phase B consisted of 0.2% formic acid in acetonitrile. Compound I assay range was 0.0125 to 25 μg/mL (0.5 mg/kg cohort) and 0.0058 to μg/mL (3.0 mg/kg cohort).

Male non-naïve beagle dogs (N=6, two groups of 3), having body weights of 9.00-11.1 kg and 10.6-13.4 kg, received an IV dose of Compound I at 0.1 mg/kg (Group I) and 1.0 mg/kg (Group II) as part of a dosing cassette. Compound I was dissolved in PEG-200:ethanol:water (40:10:50) at either a concentration of 0.2 mg/mL for dosing at 0.1 mg/kg or at a concentration of 2 mg/mL for intravenous dosing at 1 mg/kg and sterile filtered prior to administration. The dogs had access to food on their typical feeding schedules before and after administration of Compound I. Urine samples were collected on wet ice or cold packs into pre-weighed containers that were prefilled with glacial acetic acid. The samples were weighed again and additional glacial acetic acid was added if needed to a final concentration of 2%. The samples were frozen and stored (−80° C.) prior to bioanalysis.

Dog urine concentrations of Compound I were determined by LC/MS/MS. Urine study samples (diluted in $K_2$EDTA beagle dog plasma, Biochemed, Winchester, Va.) were thawed and vortexed and either 10 or 20 μL was placed in a 96-well plate. The samples were extracted with a 6-fold greater volume of acetonitrile (60 or 120 μL) with internal standard chrysin or glyburide. The extract was centrifuged for 5 minutes at 3000 RPM and ~70% of the supernatant (50 or 100 μL) was transferred to a new 96-well plate and combined with an equal volume of water. Samples were injected onto either a Mac Mod Ace C18 (2.1×50 mm, 3 μm) or a Waters Acquity UPLC BEH C18 (50×2.1 mm, 1.7 μm) column with a flow rate of either 0.8 or 0.9 mL/min. Mobile phase A consisted of 95:5:0.1 (v:v:v) water:acetonitrile:formic acid and mobile phase B consisted of 50:50:0.1 (v:v:v) methanol:acetonitrile:formic acid. Compound I assay range in urine was 0.0002 to 1.00 μg/mL.

Male non-naïve cynomolgus monkeys (N=3), having body weights of 2.87-3.61 kg, received an IV dose of Compound I at 1 mg/kg. Compound I was dissolved in 5% NaHCO$_3$ in D5W (pH 7.4) and filtered through a 0.22 μM polyvinyl difluoride (PVDF) syringe filter (Millipore Millex-GV, SLGV033RB) prior to administration. Formulations were prepared the day prior to dosing and stored at −70° C. overnight and thawed prior to dosing. Intravenous doses of Compound I were administered through an indwelling catheter in the cephalic vein followed by a saline flush of approximately 3 mL. Intravenous doses were administered at a volume of 1 mL/kg. Urine samples were collected on wet ice or cold packs into tubes containing glacial acetic acid to stabilize any potential glucuronide conjugates. Total urine sample volumes were estimated gravimetrically and aliquots were obtained and frozen (−70° C.) prior to bioanalysis.

Monkey urine concentrations of Compound I were determined by LC/MS/MS. Urine samples were thawed and diluted 5-fold in $K_2$EDTA monkey plasma (Bioreclamation, Westbury, N.Y.). The samples were vortexed and 50 μL was transferred to a 96-well plate. Samples were then extracted with 200 μL of acetonitrile with internal standard. The extract was centrifuged for 10 minutes at 2809 RPM and 50 μL of supernatant was added to 200 μL 0.2% formic acid in water. The samples (10-15 μL) were injected on a Thermo-Fisher HyPURITY™ (C18 50×2.1 mm) column with a flow rate of 0.35 mL/min. Mobile phase A consisted of 0.2% formic acid in water and mobile phase B consisted of 0.2% formic acid in acetonitrile. Compound I assay range was 0.00125 to 5 μg/mL.

The mean amount of urine excreted over a collection period of 24 h and the approximate % of administered dose excreted in urine is reported in the table below.

| Species | Amount of IV Administration (mg/kg) | Urinary Excretion (approximate % of administered dose excreted in urine) Mean$^a$ (±SD$^b$) |
|---|---|---|
| Rat | 0.5 | <0.03 (NA) |
| Rat | 3.0 | <0.02 (NA) |
| Dog | 0.1 | <0.02 (NA) |
| Dog | 1.0 | <0.001 (NA) |
| Monkey | 1.0 | 0.670 (0.593) |

$^a$Average of three determinations
$^b$Standard deviation

The renal excretion of Compound I in the rat was less than 0.02% or less than 0.03% of the administered dose, in the dog was less than 0.02% or less than 0.001% of the administered dose and in the monkey approximately 0.670%±0.593% of the administered dose. These data indicate that Compound I has low renal excretion in the three species tested.

Assay 3: Phase 1 Single-Ascending Dose Study

A Phase 1 single-ascending dose (SAD) clinical trial of Compound I' (Form I), which converts to or dissolves to provide its soluble form Compound I in the body, was conducted in order to assess neprilysin inhibition for the treatment of a range of cardiovascular and renal diseases, including, e.g., chronic kidney disease, diabetic nephropathy, acute and chronic heart failure, heart failure with reduced ejection fraction, heart failure with preserved ejection fraction, post-myocardial infarction asymptomatic left ventricular dysfunction (post-MI asymptomatic LVD), subacute heart failure and resistant and isolated systolic hypertension. Safety and tolerability, pharmacokinetic (support for QD/BID dosing and non-renal excretion), pharmacodynamic (test for target engagement biomarkers cGMP and ANP), food effect, and absolute oral bioavailability and renal elimination using a $^{14}$C intravenous microtracer, inter alia, were tested.

The Phase 1 study was a double-blind, randomized placebo-controlled single ascending dose study in healthy male and female volunteers randomized in a 4:1 ratio. The study enrolled 56 healthy volunteers over multiple weeks for the ascending-dose portion, which included cohorts (n=10/cohort of 8 active and 2 placebo) administered single ascending doses of 50 mg, 100 mg, 200 mg, 400 mg and 600 mg. A sixth cohort (n=6) was administered i.v. microtracer and oral doses of 10 μg and 100 mg, respectively. The SAD clinical trial data demonstrated in part that Compound I was well-tolerated after single doses up to 600 mg.

Assay 3.1: NEP Activity in Human (cGMP)

One goal of this study was to determine the mechanism/duration of action of Compound I after dosing in humans. To do this, levels of cGMP, a biomarker of neprilysin target engagement, were measured after dosing with Compound I' to provide evidence of the biological effect of Compound I. For example, elevation of plasma cGMP levels 24 h after dosing indicates a sustained duration of the pharmacologic effect, analogous to plasma clearance values to demonstrate pharmacokinetic persistence.

Figure 6:
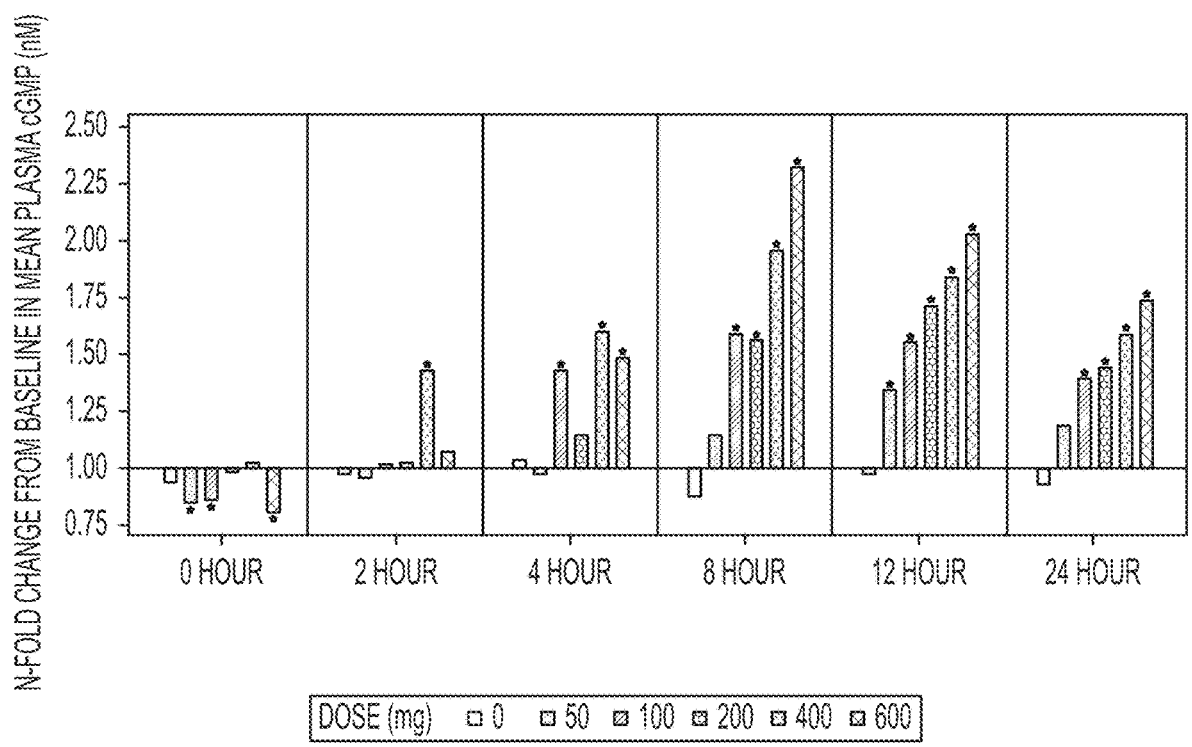
FIG. 6 shows change from baseline in mean plasma cGMP (nM) in healthy subjects receiving either no dose or a single dose of 50 mg, 100 mg, 200 mg, 400 mg and 600 mg over 24-hours.
Figure 7:
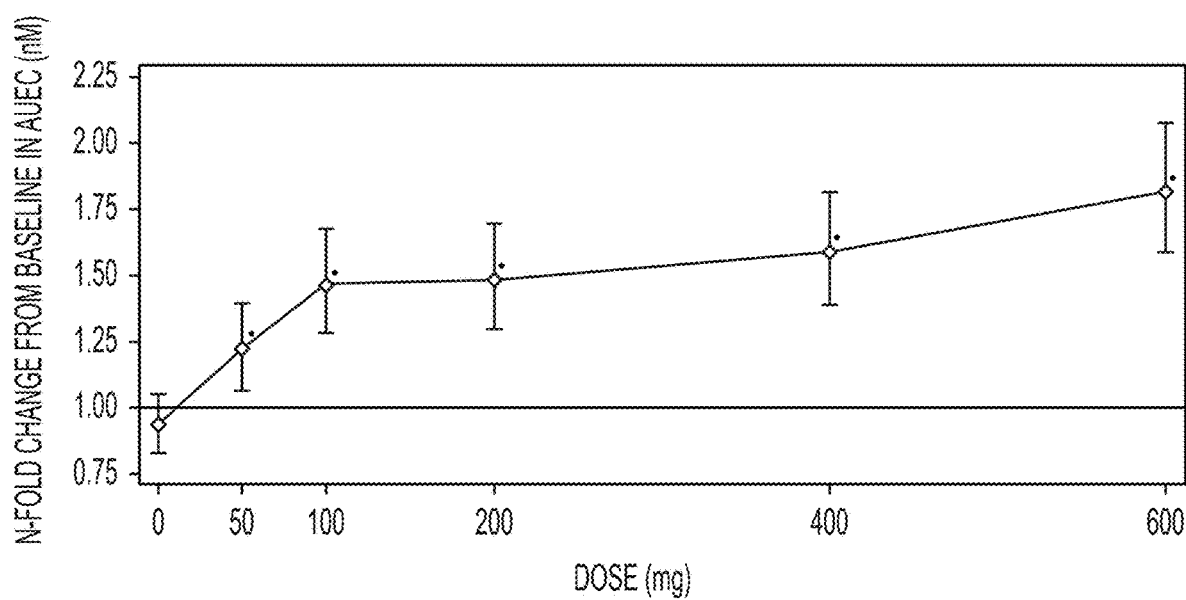
FIG. 7 illustrates n-fold change in cGMP from baseline versus dose (mg) for data generated in single ascending dose study.

FIG. 6 illustrates the change in mean plasma cGMP (nM) from baseline at the tested doses versus time. This data demonstrates that Compound I provides a sustained increase in mean plasma cGMP over 24-hours after a single dose, with a maximum level of cGMP occurring in the 8 h to 24 h range, with 8-12 h window being the highest cGMP levels. Additionally, the plasma cGMP dose response demonstrates near maximal effect at the lower end of the dose range, i.e., at dose levels ≥100 mg (see FIG. 7).

Figure 8:
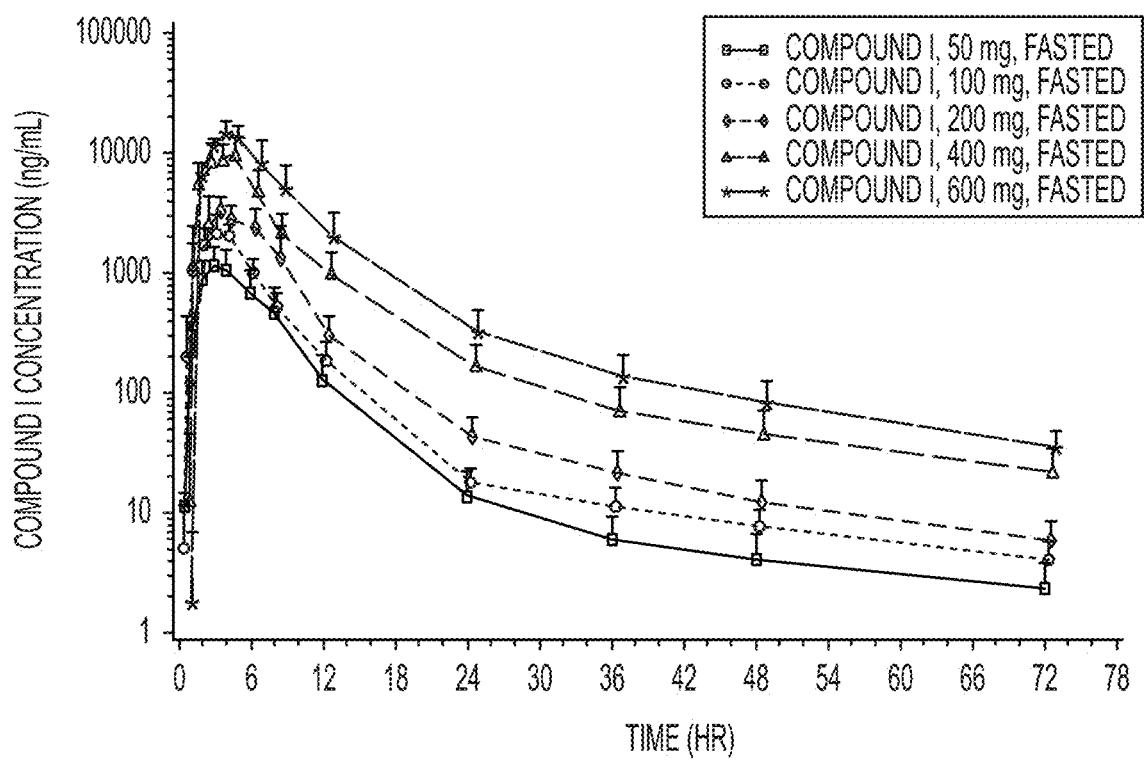
FIG. 8 is the concentration of Compound I (ng/mL) versus time (hr) for data generated in single ascending dose study.

Assay 3.2 PK Profile, Oral Bioavailability and Renal Excretion of Compound I' in Human The pharmacokinetic profile of Compound I was dose-proportional (see FIG. 8) and Compound I was shown to have high oral bioavailability (around 80%). Data from the SAD clinical trial also suggested low levels of renal elimination, i.e., less than 1% of the total Compound I' administered dose was eliminated through the kidneys as confirmed by intravenous microtracer testing technology.

Interestingly, the PK profile (e.g. $C_{max}$ of Compound I) and PD profile (e.g. $cGMP_{max}$) demonstrated peak values within different time windows. The data from the SAD clinical trial suggested dose-related increases in levels of plasma cGMP and sustained elevations of cGMP over 24 h in both plasma and urine, supporting the use of Compound I or Compound I' for once-daily dosing.

Assay 3.3: Differentiation from Standard Treatment

Figure 9:
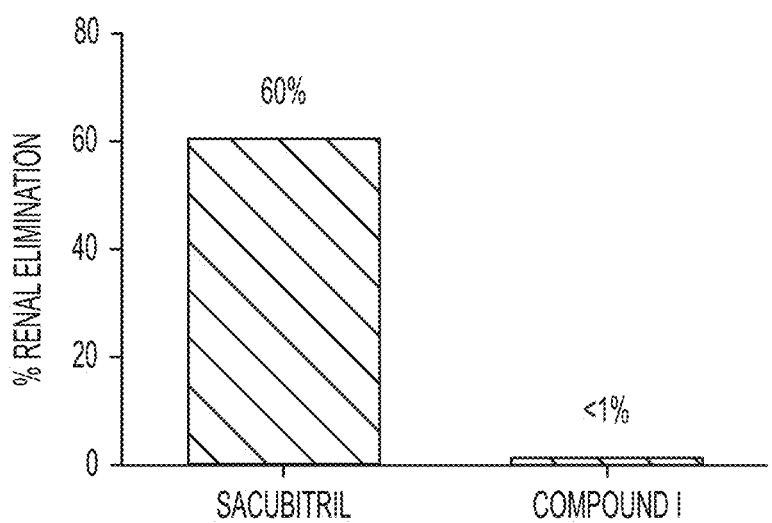
FIG. 9 shows the % renal elimination of sacubitril versus Compound I in healthy subjects.

Currently, sacubitril used in combination with valsartan is indicated to reduce the risk of cardiovascular death and hospitalization for heart failure in patients with chronic heart failure and reduced ejection fraction. A comparison of sacubitril (a neprilysin inhibitor) and Compound I demonstrates key differentiation in renal elimination and 24-hour target engagement. For example, sacubitril is largely eliminated through the kidneys (60% renal elimination) whereas Compound I is not (<1% renal elimination) (see FIG. 9). This may be important for treatment of patients who are renally-compromised with or without heart disease. Additionally, the level of cGMP (i.e., target engagement) is not elevated at 24 h postdose of sacubitril, whereas the level of cGMP is after dosing with Compound I'. This allows for potential once-daily dosing of Compound I or Compound I', which is not true for sacubitril in combination with valsartan, which is a twice-daily dosing regimen.

Assay 4: Phase 1 Multiple-Ascending Dose Study

A Phase 1 multiple-ascending dose (MAD) clinical trial of Compound I' (Form I) was conducted in order to further evaluate the safety, tolerability, pharmacokinetics of Compound I and its metabolite, pharmacodynamics of Compound I, food effect, absolute oral bioavailability and renal elimination of multiple ascending oral doses of Compound I' in healthy adult and elderly subjects. As discussed below, the reported data confirms the results stemming from the SAD clinical trial.

The Phase 1 study was a double-blind, randomized placebo-controlled multiple ascending dose study in healthy male and female volunteers randomized in a 4:1 ratio. The study enrolled 50 healthy adult (19-55 years old) and elderly (65-80 years old) volunteers over multiple weeks for the ascending-dose portion, which included cohorts (n=10/cohort of 8 active and 2 placebo) administered (1) ascending doses of 50 mg, 100 mg, and 200 mg, (2) a dose of 10 mg studied in parallel with 200 mg for PK/PK, and (3) a dose of 100 mg for one elderly cohort. The MAD clinical trial data demonstrated in part that Compound I was generally well-tolerated after multiple oral doses up to 14 days. Additionally, renal elimination of Compound I was neglible after multiple dosing, e.g., <1% was observed on Day 1 and Day 14 for all subjects.

Assay 4.1: NEP Activity in Human (cGMP) and Differentiation from Standard Treatment Part of the MAD clinical studies was to determine the mechanism/duration of action of Compound I after dosing in humans. To do this, levels of cGMP, a biomarker of neprilysin target engagement, were measured after dosing with Compound I' to provide evidence of the biological effect of Compound I. For example, elevation of plasma cGMP levels 24 h after dosing indicates a sustained duration of the pharmacologic effect, analogous to plasma clearance values to demonstrate pharmacokinetic persistence.

Figure 10:
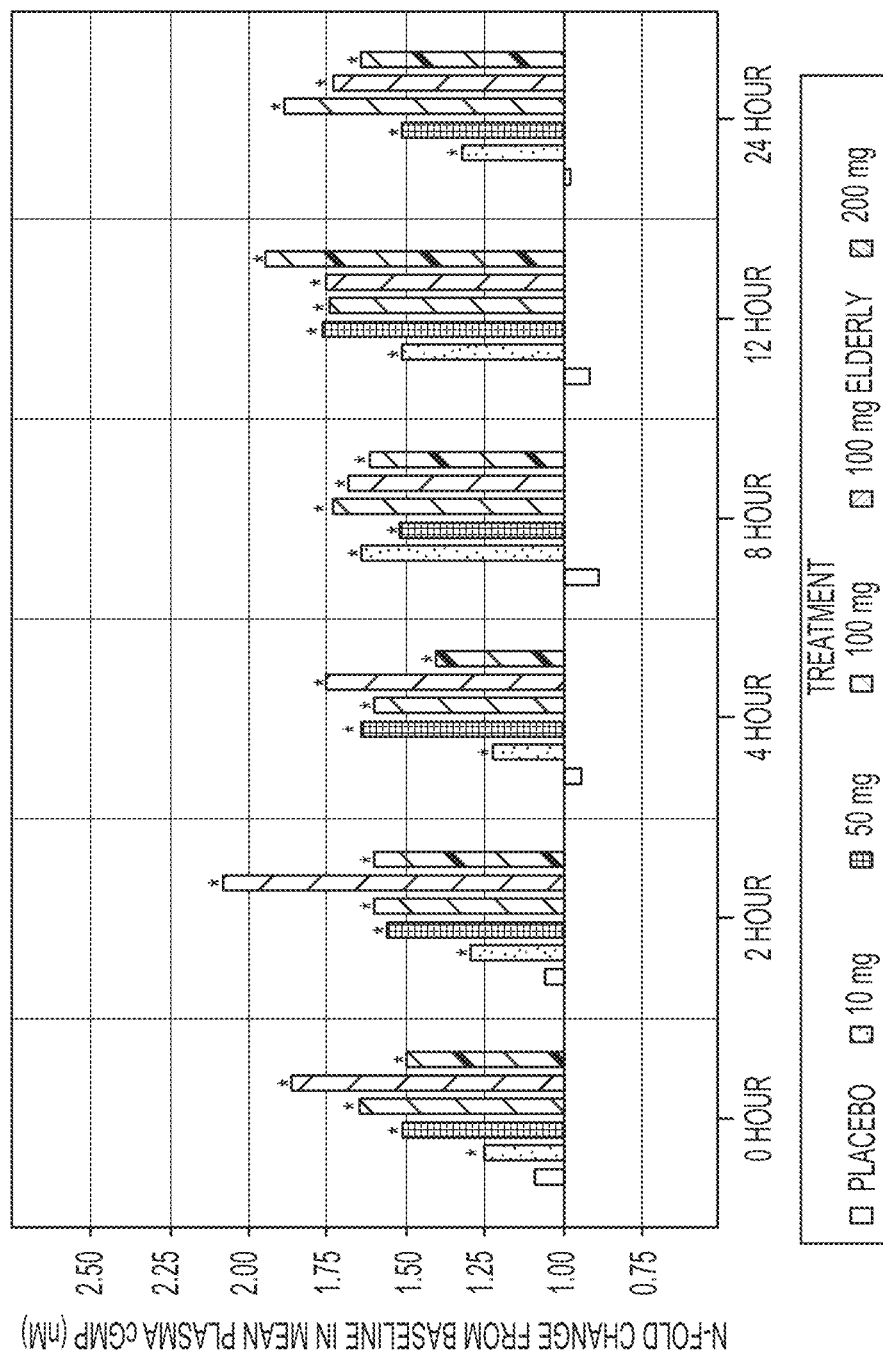
FIG. 10 shows shows change from baseline in mean plasma cGMP (nM) at Day 14 in healthy adult and elderly subjects receiving either no dose or a single dose of 10 mg, 50 mg, 100 mg, and 200 mg over 24-hours.

FIG. 10 illustrates the change in mean plasma cGMP (nM) from baseline at the tested doses versus time. This data demonstrates that Compound I provides a sustained increase in mean plasma cGMP over 24 h. An important result is shown in FIG. 10. This data illustrates that on Day 14 of the clinical study, there was target engagement of all doses at trough (0 h) as well as all doses measured up to 24 h for a once-daily dose of Compound I'. This is in contrast to standard treatment where there is little to no target engagement at trough and 24 h with a twice-daily dosing regimen (see page 411 of Gu et al., J. Clin. Pharmacol., 2010, Vol. 50, Issue 4, pp. 401-414).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A process for preparing (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I), the process comprising:
   (a) coupling benzyl (2S,4R)-4-amino-5-(5'-chloro-2'-fluoro-[1,1'-biphenyl]-4-yl)-2-(ethoxymethyl)-2-methylpentanoate hydrochloride with 3-((4-methoxybenzyl)oxy)isoxazole-5-carboxylic acid in a solvent in approximately a 1:1 molar ratio to give benzyl (2S, 4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate; and (b) deprotecting benzyl (2S,4R)-5-(5'-chloro-2'-fluoro-[1,1'-biphenyl]-4-yl)-2-(ethoxymethyl)-4-(3-((4-methoxybenzyl)oxy)isoxazole-5-carboxamido)-2-methylpentanoate to form (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I).

2. The process of claim 1, wherein (a) further comprises a peptide coupling agent and a base in approximately a 1:3:1:1 molar ratio of coupling agent to base to benzyl (2S,4R)-4-amino-5-(5'-chloro-2'-fluoro-[1,1'-biphenyl]-4-yl)-2-(ethoxymethyl)-2-methylpentanoate hydrochloride to 3-((4-methoxybenzyl)oxy)isoxazole-5-carboxylic acid.

3. The process of claim 2, wherein the coupling agent is 2-(6-chloro-1H-benzo[d][1,2,3]triazol-1-yl)-1,1,3,3-tetramethyluronium hexafluorophosphate(V) and the base is N,N-diisopropylethylamine.

4. The process of claim 1, wherein (b) is performed with a palladium catalyst and hydrogen gas.

5. The process of claim 1, wherein (a) further comprises a peptide coupling agent.

6. The process of claim 5, wherein the peptide coupling agent is selected from O-(benzotriazol-1-yl)-N,N,N',N'-tetramethyluronium hexafluorophosphate, O-(benzotriazol-1-yl)-N,N,N',N'-tetramethyluronium tetrafluoroborate, O-(7-azabenzotriazol-1-yl)-N,N,N',N'-tetramethyluronium hexafluorophosphate, O-(7-azabenzotriazol-1-yl)-N,N,N',N'-tetramethyluronium tetrafluoroborate, O-(6-chlorobenzotriazol-1-yl)-N,N,N',N'-tetramethyluronium hexafluorophosphate, and O-[(ethoxycarbonyl)cyanomethylenamino]-N,N,N',N'-tetra methyluronium tetrafluoroborate.

7. The process of claim 6, wherein the peptide coupling agent is selected from O-(benzotriazol-1-yl)-N,N,N',N'-tetramethyluronium hexafluorophosphate, O-(7-azabenzotriazol-1-yl)-N,N,N',N'-tetramethyluronium hexafluorophosphate, and O-(6-chlorobenzotriazol-1-yl)-N,N,N',N'-tetramethyluronium hexafluorophosphate.

8. The process of claim 7, wherein the peptide coupling agent is O-(6-chlorobenzotriazol-1-yl)-N,N,N',N'-tetramethyluronium hexafluorophosphate.

9. The process of claim 1, wherein (a) further comprises a base.

10. The process of claim 9, wherein the base is N,N-diisopropylethylamine.

11. The process of claim 1, wherein the solvent of (a) is tetrahydrofuran.

12. The process of claim 1, wherein the deprotecting of (b) comprises adding a palladium catalyst.

13. The process of claim 1, wherein the deprotecting of (b) comprises adding hydrogen.

14. The process of claim 1, wherein the deprotecting of (b) comprises adding ethanol.

15. The process of claim 12, further comprising removing the palladium catalyst following the deprotecting of (b).

16. The process of claim 15, further comprising adding an oxidizing agent following the removing of the palladium catalyst.

17. The process of claim 16, wherein the oxidizing agent is hydrogen peroxide.

18. The process of claim 8, wherein (a) further comprises N,N-diisopropylethylamine.

19. The process of claim 18, wherein the deprotecting of (b) comprises adding a palladium catalyst and hydrogen.

20. The process of claim 1, further comprising isolating (2S,4R)-5-(5'-chloro-2'-fluoro-[1,1'-biphenyl]-4-yl)-2-(ethoxymethyl)-4-(3-hydroxyisoxazole-5-carboxamido)-2-methylpentanoic acid (I).

* * * * *